United States Patent [19]

Fukuoka et al.

[11] Patent Number: 4,621,149

[45] Date of Patent: Nov. 4, 1986

[54] PRODUCTION OF URETHANE COMPOUNDS

[75] Inventors: Shinsuke Fukuoka; Masazumi Chono, both of Kurashiki, Japan

[73] Assignee: Asahi Kasei Kogyo Kabushiki Kaisha, Japan

[21] Appl. No.: 681,061

[22] Filed: Dec. 10, 1984

Related U.S. Application Data

[63] Continuation of Ser. No. 451,887, Dec. 21, 1982, abandoned.

[30] Foreign Application Priority Data

| Dec. 25, 1981 | [JP] | Japan | 56-213191 |
| Dec. 30, 1981 | [JP] | Japan | 56-210640 |
| Jan. 19, 1982 | [JP] | Japan | 57-5356 |
| Jan. 19, 1982 | [JP] | Japan | 57-5357 |
| Jan. 25, 1982 | [JP] | Japan | 57-8840 |
| Jan. 25, 1982 | [JP] | Japan | 57-8841 |
| Jan. 28, 1982 | [JP] | Japan | 57-10862 |
| Jan. 28, 1982 | [JP] | Japan | 57-10863 |
| Jan. 28, 1982 | [JP] | Japan | 57-10864 |
| Jan. 28, 1982 | [JP] | Japan | 57-10865 |
| Feb. 5, 1982 | [JP] | Japan | 57-16442 |
| Feb. 22, 1982 | [JP] | Japan | 57-26144 |
| Feb. 22, 1982 | [JP] | Japan | 57-26145 |
| Feb. 23, 1982 | [JP] | Japan | 57-26750 |
| Feb. 24, 1982 | [JP] | Japan | 57-27290 |
| Feb. 24, 1982 | [JP] | Japan | 57-28532 |
| Feb. 25, 1982 | [JP] | Japan | 57-28106 |
| Feb. 25, 1982 | [JP] | Japan | 57-28107 |
| Feb. 25, 1982 | [JP] | Japan | 57-29170 |
| Feb. 26, 1982 | [JP] | Japan | 57-28874 |
| Feb. 26, 1982 | [JP] | Japan | 57-28875 |
| Mar. 1, 1982 | [JP] | Japan | 57-30579 |
| Mar. 3, 1982 | [JP] | Japan | 57-32213 |
| Mar. 15, 1982 | [JP] | Japan | 57-39349 |
| Mar. 15, 1982 | [JP] | Japan | 57-39350 |
| Mar. 24, 1982 | [JP] | Japan | 57-45667 |
| Mar. 26, 1982 | [JP] | Japan | 57-48324 |

[51] Int. Cl.$^4$ .............. C07C 125/077; C07C 125/065; C07C 125/067; C07C 125/073; C07C 125/075

[52] U.S. Cl. .................... 560/24; 560/25; 560/157; 560/158; 560/115; 560/28; 560/22; 560/13; 560/9; 560/26; 560/166; 560/32; 560/162; 560/163; 560/165; 560/33; 548/531; 548/573; 546/245; 544/172; 544/386; 549/484

[58] Field of Search .............. 560/24, 25, 157, 158, 560/115, 28, 22, 13, 9, 26, 166, 32, 162, 163, 165, 33; 548/531, 573; 546/245; 544/172, 386; 549/484

[56] References Cited

U.S. PATENT DOCUMENTS

| 3,531,512 | 9/1970 | Hardy et al. | 560/25 |
| 3,641,092 | 2/1972 | Henry et al. | 560/157 X |
| 4,178,455 | 12/1979 | Hirai et al. | 560/24 |
| 4,227,008 | 10/1980 | Miyata et al. | 560/25 |
| 4,297,501 | 10/1981 | Becker et al. | 560/24 |
| 4,304,922 | 12/1982 | Becker et al. | 560/24 |
| 4,319,035 | 3/1982 | Merger et al. | 560/25 |

FOREIGN PATENT DOCUMENTS

0036895  10/1981  European Pat. Off.

*Primary Examiner*—Bernard Helfin
*Attorney, Agent, or Firm*—Wyatt, Gerber, Shoup, Scobey and Badie

[57] ABSTRACT

A process for producing a urethane compound which comprises reacting at least one compound selected from the group consisting of a primary amine, a secondary amine and a urea compound with carbon monoxide and an organic hydroxyl compound in the presence of a catalyst system comprising:

(a) at least one member selected from the group consisting of platinum group metals and compounds containing at least one platinum group element; and (b) at least one halogen-containing compound selected from the group consisting of alkali or alkaline earth metal halides, onium halides, compounds capable of forming onium halides in the reaction, oxo acids of halogen atoms and their salts, complex compounds containing halogen ions, organic halides and halogen molecules, in the presence of molecular oxygen and/or an organic nitro compound as an oxidizing agent at a temperature of from about 80° C. to about 300° C. under a pressure of from about 1 Kg/cm$^2$ to about 500 Kg/cm$^2$.

41 Claims, No Drawings

PRODUCTION OF URETHANE COMPOUNDS

RELATED APPLICATION

This application is a continuation application of application Ser. No. 451,887, filed Dec. 21, 1982 and now abandoned.

DESCRIPTION

1. Technical Field

This invention relates to the production of urethane compounds. More particularly, it relates to processes for producing urethane compounds by oxidative carbonylation which comprise reacting at least one compound selected from the group consisting of a primary amine, a secondary amine and a urea compound with carbon monoxide and an organic hydroxyl compound in the presence of an oxidizing agent and a specified catalyst system.

2. Background Art

Urethane compounds are important compounds useful for carbamate type agricultural medicines, and for conversion to isocyanate compounds by thermal decomposition. Such compounds have heretofore been available principally by reactions involving dangerous phosgene. Thus, it is desired to produce urethane compounds as the starting materials for the production of isocyanate compounds without using phosgene, and to do so at low cost.

Heretofore, there have been proposed mainly two methods for the production of urethane compounds using carbon monoxide. More specifically, one method comprises reductively urethanating a nitro compound in the presence of an alcohol. For example, in the case of nitrobenzene, the reaction may be represented by the following equation:

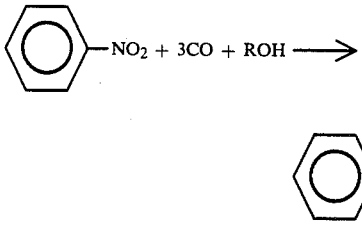

wherein R represents an organic group.

In this reaction, however, 3 mols of carbon monoxide are required per mol of nitrobenzene and two mols of the carbon monoxide are converted to carbon dioxide of no value. Thus, a disadvantage of the process is that only ⅓ of carbon monoxide is effectively employed. Moreover, in order continuously to carry out this reaction, carbon dioxide must be separated from a gaseous mixture of carbon monoxide and carbon dioxide. This compounds the difficulties of commercial practice of the method.

The other method comprises oxidatively urethanating by reacting a primary amino compound or a N,N'-disubstituted urea with carbon monoxide and an alcohol in the presence of oxygen or an oxidizing agent such as an organic nitro compound. This method has advantages compared to the above described method since carbon monoxide is effectively utilized. However, it is required that a chloride of an element which is a Lewis acid and yet capable of performing redox reaction, such as cupric chloride, ferric chloride, iron oxychloride, vanadium chloride and vanadium oxychloride, be dissolved in the reaction system as a promoter (see U.S. Pat. No. 4,297,501; European Pat. No. 36,895; and U.S. Pat. No. 4,304,922). Solutions of these chlorides are highly corrosive to metallic materials of reaction vessels, pipelines and valves. As a result, expensive metallic materials must be used. Further, when an aromatic urethane compound is produced, complicated and expensive procedures are required for the separation and recovery of these chlorides which are dissolved in the high boiling aromatic products such as aromatic urethanes or diarylureas. In addition, these promoters cannot be completely regenerated even by reoxidation in the reaction system since the hydrogen chloride formed in the redox reaction is converted to a hydrochloride of unreacted amine. As a result, there is partially reduced catalyst in the catalyst recovered. Therefore these promoters must be freshly prepared for each reaction.

Thus, there has been an urgent need to develop a new process which will avoid the above described problems, and extensive studies have been conducted to achieve this result.

DISCLOSURE OF THE INVENTION

The present invention in one embodiment provides processes for producing urethane compounds which comprise reacting at least one compound selected from the group consisting of a primary amine, a secondary amine and a urea compound with carbon monoxide and an organic hydroxyl compound in the presence of a catalyst system comprising:

(a) at least one member selected from the group consisting of platinum group metals and compounds containing at least one platinum group element; and (b) at least one halogen-containing compound selected from the group consisting of alkali or alkaline earth metal halides, onium halides, compounds capable of forming onium halides in the reaction, oxo acids of halogen atoms and their salts, complex compounds containing halogen ions, organic halides and halogen molecules, in the presence of molecular oxygen and/or an organic nitro compound as an oxidizing agent at a temperature of from about 80° C. to about 300° C. at a pressure of from about 1 Kg/cm² to about 500 Kg/cm².

The present invention in another embodiment provides processes for producing urethane compounds which comprise reacting at least one compound selected from the group consisting of a primary amine, a secondary amine and a urea compound with carbon monoxide and an organic hydroxyl compound in the presence of a catalyst system comprising (c) a basic substance as an additional promoter in addition to the above described components (a) and (b) in the presence of molecular oxygen or an organic nitro compound at a temperature of from about 80° C. to about 300° C. at a pressure of from about 1 Kg/cm² to about 500 Kg/cm².

Using the catalyst systems of this invention, urethane compounds can be obtained from primary or secondary amines and urea compounds with a high selectivity and a high yield.

In the catalyst system of this invention, the halogen atom in the halogen-containing compound plays an important role as a promoter. The preferred halogen atoms are bromine and iodine, and iodine is more preferred.

Such a fact is entirely unexpected from the prior art documents as described above (U.S. Pat. No. 4,297,501; European Pat. No. 36,895 and U.S. Pat. No. 4,304,922).

More specifically, in the prior art references a catalyst comprising, as the main catalyst, a platinum group compound and, as a promoter, a chloride of an element capable of performing redox reaction in the reaction system is employed. As the representative example there is described a combination of palladium chloride and ferric chloride or a trivalent iron such as iron oxychloride. In such a system, the principal product of urethane compound may be considered to be produced according to the so called Wacker reaction type catalyst cycle wherein divalent palladium participates in the reaction and is reduced as the reaction progresses to zero valence palladium which is then re-oxidized with trivalent iron to form divalent palladium simultaneously with reduction of trivalent iron to divalent iron, which divalent iron is oxidized again with an oxidizing agent to be returned to trivalent iron.

Thus, in the method of the prior art references it is apparent that the chloride of an element which will undergo redox action in the reaction system is essential as the re-oxidizing agent for the main catalyst. As the element having such a function, there are mentioned those susceptible of redox reaction selected from the elements of Group IIIa to Va and Group Ib to VIIIb in the Periodic Table, more specifically, such as copper, zinc, mercury, thallium, tin, titanium, arsenic, antimony, bismuth, vanadium, chromium, molybdenum, tungsten, manganese, iron, cobalt and nickel. Of these elements, only copper, vanadium, manganese, molybdenum, tungsten, antimony and iron are employed for the urethanation of an aromatic primary amine or an aromatic urea compound. There is no example for the urethanation of an aliphatic or alicyclic primary or secondary amine or an urea compound.

In contrast, the method of this invention employs specifically selected halogen-containing compounds and, if necessary or if desired, a basic substance as an additional promoter. It is completely unnecessary to employ a metal element such as described above which will undergo redox action in the reaction system. It is rather preferred not to utilize such heavy metals for more smoothly advancing the reaction. Furthermore, in the previously known processes a chlorine ion is essential as an activator of the metal element having redox action, while in the reaction of the present invention, chlorine is not essential. In fact, bromine and iodine are preferred and iodine is especially preferred since bromine and iodine appear to give higher yields, and iodine gives the highest. For these reasons, the reactions of this invention are clearly different from the reaction disclosed in the prior art.

It may be possible that the halogen-containing compound according to this invention contain the above described elements as one constituting component.

The mechanism by which the halogen-containing compound which can be employed in this invention participates in the reaction is not clear. However, in combination with platinum group metals or compounds containing platinum group elements, they clearly play important roles as the catalyst components for the oxidative urethanation of primary and secondary amines and urea compounds. This is apparent from the fact that when only the halogen-containing compound is used or such a compound in combination with a basic substance as an additional promoter, the urethanation reaction does not take place. Also, if only the platinum group metal or a compound containing the platinum group element is employed, the urethanation hardly proceeds under the reaction conditions of this invention, or if there is a reaction, only a small amount of urethane compound is produced. Particularly, when only a metallic platinum group metal is used, harly any urethane compound is obtained. For example, with the use of palladium black alone which is a metallic palladium with zero valency, there is practically no reaction although palladium is one of the more effective catalyst components when employed in accordance with the reaction of this invention. However, together with a halogen-containing compound such as cesium iodide or tetramethylammonium iodide or with a combination of the halogen-containing compound and a basic substance such as a combination of iodine and trimethylamine, or a combination of iodoform and rubidium hydroxide, it is possible to obtain close to a quantitative yield of urethane compound. There is a particular advantage of the processes of this invention compared to the known processes in which a platinum group metal or compound is employed together with a Lewis acid such as ferric chloride. In the prior art process, the platinum or platinum group compound is eluted out with the acid into the reaction mixture. Recovery is a cumbersome and expensive procedure. In contrast, according to the method of this invention, substantially no platinum group metal is eluted out into the reaction mixture and thus, the expensive platinum group catalyst components can easily be separated and recovered, for example, by filtration. The importance of this advantage in commercial practice will be readily apparent to those skilled in the art.

The use of a basic substance as an additional promoter markedly improves the yield and the selectivity of urethane compounds in accordance with the process of this invention.

Any of a large selection of platinum group metals or compounds containing a platinum group element can be used in the process of the present invention. These include, for example, palladium, rhodium, platinum, ruthenium, iridium and osmium, metal blacks thereof and compounds containing these elements. These catalysts may be supported on any of a number of known carriers such as active carbon, graphite, silica, alumina, silica-alumina, silica-titania, titania, zirconia, barium sulfate, calcium carbonate, asbestos, bentonite, diatomaceous earth, polymers, ion-exchange resins, zeolite, molecular sieve, magnesium silicate and magnesia.

Metallic catalysts may be prepared by supporting compounds containing these metal ions on a carrier and reducing them with hydrogen or formaldehyde. Alloys and intermetallic compounds containing these metals may also be employed. These may include those between these platinum group metals or those containing other elements such as selenium, tellurium, sulfur, antimony, bismuth, copper, silver, gold, zinc, tin, vanadium, iron, cobalt, nickel, mercury, lead, thallium, chromium, molybdenum and tungsten.

Exemplary compounds containing platinum group elements which may be employed include inorganic acid salts such as the halides, sulfates, nitrates, phosphates and borates; organic acid salts such as the acetates, oxalates and formates; cyanides; hydroxides; oxides, sulfides; metal acid salts containing an anion such as a nitro group, a cyano group, a halogen atom and an oxalate ion; metal complexes with salts or complexes containing ammonia, an amine, a phosphine and a carbon monoxide ligand; and organometallic compounds having an organic ligand or an organic group.

Of these catalyst components, those containing palladium or rhodium or both are particularly preferred. Suitable examples of such components include Pd black; carrier-supported palladium catalysts such as Pd-C, Pd-Al$_2$O$_3$, Pd-SiO$_2$, Pd-TiO$_2$, Pd-ZrO$_2$, Pd-BaSO$_4$, Pd-CaCO$_3$, Pd-asbestos, Pd-zeolite and Pd-molecular sieve; alloys and intermetallic compounds such as Pd-Pb, Pd-Se, Pd-Te, Pd-Hg, Pd-Tl, Pd-P, Pd-Cu, Pd-Ag, Pd-Fe, Pd-Co, Pd-Ni and Pd-Rh and these alloys and intermetallic compounds supported on the carrier as described above; inorganic acid salts such as PdCl$_2$, PdBr$_2$, PdI$_2$, Pd(NO$_3$)$_2$ and PdSO$_4$; organic acid salts such as Pd(OCOCH$_3$)$_2$ and palladium oxalate; Pd(CN)$_2$; PdO; PdS; palladium acid salts represented by M$_2$(PdX$_4$) and M$_2$(PdX$_6$) wherein M represents an alkali metal, an ammonium ion, a nitro group or a cyano group and X represents a halogen atom; amine complexes represented by [Pd(NH$_3$)$_4$]X$_2$ and [Pd(en)$_2$]X$_2$ where X is the same as defined above and en represents ethylenediamine; complex compounds or organometallic compounds such as PdCl$_2$-(PhCN)$_2$, PdCl$_2$(PR$_3$)$_2$, Pd(CO)(PR$_3$)$_3$, Pd(PPh$_3$)$_4$, PdCl(R)-(PPh$_3$)$_2$, Pd(C$_2$H$_4$)(PPh$_3$)$_2$ and Pd(C$_3$H$_5$)$_2$ where R represents an organic group and Ph represents a phenyl group; complex compounds having a coordinated chelate ligand such as Pd(acac)$_2$ where acac represents an acetylacetonato group; rhodium black; carrier-supported rhodium catalysts similar to those of Pd; rhodium alloys and intermetallic compounds which may be supported on a carrier similar to those of Pd; inorganic acid salts such as RhCl$_3$ and its hydrates, RhBr$_3$ and its hydrates, RhI$_3$, its hydrates and Rh$_2$(SO$_4$)$_3$ and its hydrates; Rh$_2$(OCOCH$_3$)$_4$, Rh$_2$O$_3$, RhO$_2$, M$_3$(RhX$_6$) and hydrates thereof wherein M and X are the same as defined above; amine complexes of rhodium such as [Rh(NH$_3$)$_5$]X$_3$ and [Rh(en)$_3$]X$_3$; rhodium carbonyl clusters such as Rh$_4$-(CO)$_{12}$ and Rh$_6$(CO)$_{16}$; complex compounds or organometallic compounds such as [RhCl(CO)$_2$]$_2$, RhCl$_3$(PR$_3$)$_3$, RhCl(PPh$_3$)$_3$, RhX(CO)L$_2$ where X is the same as defined above, L is a ligand comprising an organic phosphorous compound and an organic arsenic compound and Ph is a phenyl group; and RhH(CO)(PPh$_3$)$_3$ where Ph is a phenyl group. In this invention there may be employed either one kind of these platinum group metals or compounds containing platinum group elements or a mixture of two or more kinds thereof.

The amount of the platinum group element or compound containing a platinum group element which may be employed in this invention is not particularly limited. The amount of the platinum group element per se or in its compound is typically about 0.0001 to about 50% by mol per mol of the primary amine, secondary amine and/or urea compound employed.

The halogen-containing compounds which can be used in this invention include alkali metal halides, alkaline earth metal halides, onium halides, compounds capable of forming onium halides in the reaction, oxo acids of halogen atoms and their salts, complex compounds containing halogen ions, organic halides and halogen molecules.

Exemplary alkali metal halides and alkaline earth metal halides include single salts such as sodium fluoride, cesium fluoride, barium fluoride, lithium chloride, sodium chloride, potassium chloride, rubidium chloride, cesium chloride, magnesium chloride, calcium chloride, strontium chloride, barium chloride, lithium bromide, sodium bromide, rubidium bromide, cesium bromide, magnesium bromide, strontium bromide, barium bromide, lithium iodide, sodium iodide, potassium iodide, rubidium iodide, cesium iodide, magnesium iodide, calcium iodide, strontium iodide, and barium iodide; double salts such as sodium magnesium chloride, potassium magnesium chloride, potassium calcium chloride and potassium magnesium bromide; and polyhalides such as potassium bromofluoride, potassium iodochloride, rubidium iodochloride, cesium iodochloride, cesium iodochlorobromide, rubidium iodochlorobromide, potassium iodobromide, cesium iodobromide and rubidium iodobromide.

The onium halide means a compound containing an element having a lone pair of electrons in which a proton or another cation type reagent is bonded to the lone pair of electrons to increase one covalent bond valency of the element having the lone pair of electrons to become a cation, and having a halogen anion electrovalently bound as the counter ion.

Exemplary onium halides include ammonium compounds of the formula (R$^1$R$^2$R$^3$R$^4$N$^\oplus$)X$^\ominus$, phosphonium compounds having the formula (R$^1$R$^2$R$^3$R$^4$P$^\oplus$)X$^\ominus$, arsoium compounds having the formula (R$^1$R$^2$R$^3$R$^4$As$^\oplus$)X$^\ominus$, stibonium compounds having the formula (R$^1$R$^2$R$^3$R$^4$Sb$^\oplus$)X$^\ominus$, oxonium compounds having the formula (R$^1$R$^2$R$^3$O$^\oplus$)X$^\ominus$, sulfonium compounds having the formula (R$^1$R$^2$R$^3$S$^\oplus$)X$^\ominus$, oxysulfonium compounds having the formula [R$^1$R$^2$R$^3$S$^\oplus$(O)]X$^\ominus$, selenonium compounds having the formula (R$^1$R$^2$R$^3$Se$^\oplus$)X$^\ominus$, telluronium compounds having the formula (R$^1$R$^2$R$^3$Te$^\oplus$)X$^\ominus$, stannonium compounds (R$^1$R$^2$R$^3$Sn$^\oplus$)X$^\ominus$ and iodonium compounds having the formula (R$^1$R$^2$I$^\oplus$)X$^\ominus$. In these formulae, R$^1$, R$^2$, R$^3$ and R$^4$ each independently represents a hydrogen atom or a group selected from the group consisting of aliphatic groups, aromatic groups, alicyclic groups, arylaliphatic groups and heterocyclic groups which may sometimes be a constituent of a ring containing an element having a lone pair of electrons; and X represents a halogen atom selected from the group consisting of F, Cl, Br and I. Compounds having two or more of such onium groups in the molecule and further polymers containing such onium groups in the main chain or a side chain thereof may also be employed.

Such onium halides where a halogen is an anion can readily be obtained by the reaction of a hydrogen halide or an organic halide with the counterpart amine, nitrogen-containing compound, phosphine compound, arsine compound, stibine compound, oxy compound, sulfide compound, sulfoxide compound, selenide compound or telluride compound. These onium halides may be formed either outside the reaction system or in the reaction system. Furthermore, the onium halides prepared according to other methods may also be available and they may be formed in the reaction system according to other methods.

Of these onium halides, ammonium halides, phosphonium halides, arsonium halides and sulfonium halides are preferred, and ammonium halides and phosphonium halides are the most preferred. An ammonium halide can be readily obtained by the reaction of a corresponding nitrogen-containing compound with a hydrogen halide or the reaction of a nitrogen-containing compound with an alkyl halide or an aryl halide. Such nitrogen-containing compounds include, for example, ammonia, amines such as primary amines, secondary amines and tertiary amines, hydroxylamines, hydrazines, hydrazones, amino acids, oximes, imidoesters, amides and various nitrogen-containing heterocyclic compounds.

Exemplary hydrogen halide salts of nitrogen-containing compounds which can be employed include the salts of ammonia such as ammonium chloride, ammonium bromide and ammonium iodide; the salts of aromatic amines such as diphenylamine and triphenylamine; the salts of aliphatic amines such as methylamine, ethylamine, n-hexylamine, n-octylamine, dimethylamine, trimethylamine, diethylamine, triethylamine, di-n-butylamine, tri-n-propylamine, methylethylamine, dimethylethylamine, di-n-butylmethylamine, tri-n-butylamine, ethylenediamine and hexamethylenediamine; the salts of alicyclic amines such as cyclopropylamine, cyclohexylamine and N-methylcyclohexylamine; the salts of arylaliphatic amines such as benzylamine, N-methylbenzylamine, N,N-diethylbenzylamine and dibenzylamine; the salts of nitrogen-containing heterocyclic compounds such as piperidine, piperazine, morpholine, pyridine, quinoline, hexamethyltetramine, oxazole, thiazole, imidazole, triazole, benzotriazole and diazabicycloundecene; and the salts of amides such as dimethylacetamide and N-methylpyrrolidone.

Exemplary quaternary ammonium halides which can be employed include aliphatic quaternary ammonium halides such as tetramethylammonium halides, tetraethylammonium halides, tetra-n-butylammonium halides, trimethylethylammonium halides, diethyldibutylammonium halides; alcyclic quaternary ammonium halides such as N,N,N-trimethylcyclohexylammonium halides; arylaliphatic quaternary ammonium halides such as tetrabenzylammonium halides and trimethylbenzylammonium halides; aromatic quaternary ammonium halides such as N,N,N-trimethylphenylammonium halides and N,N,N-triethylphenylammonium halides; and heterocyclic quaternary ammonium halides such as N-methylpyridinium halides, N-ethylquinolinium halides, N,N-dimethylpiperidinium halides and N,N'-dimethylimidazolinium halides.

Exemplary polymers containing an ammonium halide group in the main chain or the side chain which can also be used include polymers having main constituent units of the following formulae:

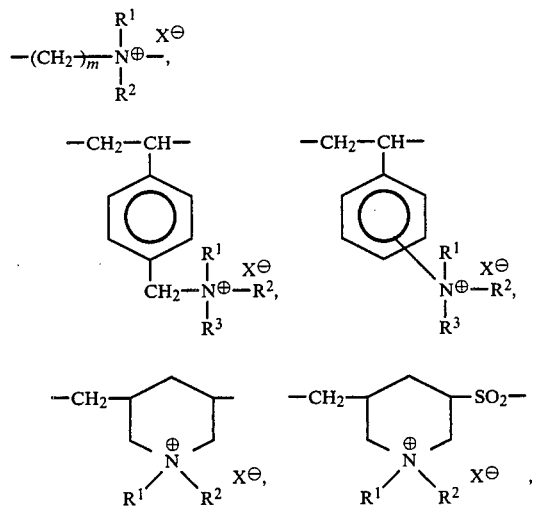

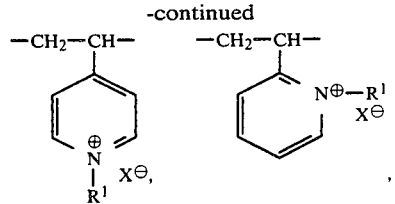

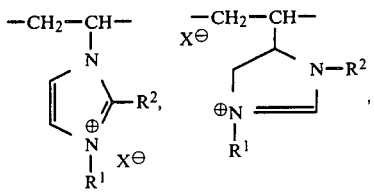

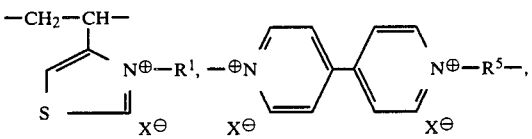

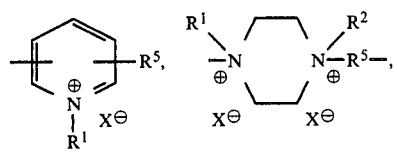

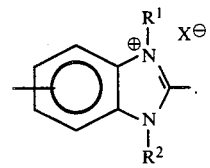

In the above described formulae, $R^1$, $R^2$, $R^3$ and X are the same as defined above, and $R^5$ represents a divalent organic group.

Exemplary phosphonium halides which can be used include symmetric tetraalkylphosphonium halides such as tetramethylphosphonium halides, tetraethylphosphonium halides and tetra-n-butylphosphonium halides; asymmetric tetraalkylphosphonium halides such as ethyltrimethylphosphonium halides and diethyldimethylphosphonium halides; symmetric tetraarylphosphonium halides such as tetraphenylphosphonium halides and tetra(p-tolyl)phosphonium halides; asymmetric tetraarylphosphonium halides such as ($\alpha$-naphthyl)-triphenylphosphonium halides; alkyl/aryl mixed phosphonium halides such as methyltriphenylphosphonium halides and phenyltrimethylphosphonium halides; and tetraaralkylphosphonium halides such as tetrabenzylphosphonium halides.

Exemplary arsonium halides which can be used include symmetric tetraalkylarsonium halides such as tetramethylarsonium halides and tetraethylarsonium halides; asymmetric tetraalkylarsonium halides such as methyltriethylarsonium halides and diethyldimethylarsonium halides; symmetric tetraarylarsonium halides such as tetraphenylarsonium halides; and alkyl/aryl mixed arsonium halides such as methyltriphenylarsonium halides, ethyltriphenylarsonium halides and phenyltrimethylarsonium halides.

Exemplary sulfonium halides which can be employed include symmetric or asymmetric alkylsulfonium halides such as trimethylsulfonium halides, triethylsulfonium halides and methyldiethylsulfonium halides; arylsulfonium halides such as triphenylsulfonium halides; alkyl/aryl mixed sulfonium halides such as dimethylphenylsulfonium halides and methyldiphenylsulfonium halides; and cyclic sulfonium halides such as bicyclo-(2,2,1)-heptane-1-sulfonium halides and thiopyrylium halides.

Polymers having a phosphonium halide group or a sulfonium halide group in the main chain or the side chain which can also be employed include polymers having main constituent units of the following formulae:

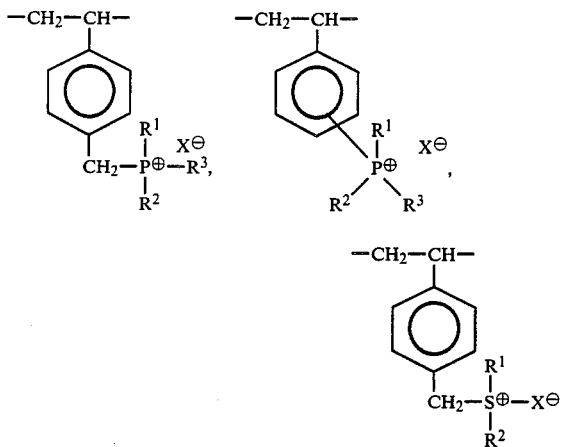

wherein $R^1$, $R^2$, $R^3$, X are the same as defined above.

The oxo acids of halogen atoms and their salts mean oxygen acids of halogen atoms with an oxidation number of +1, +3, +5 or +7 and their salts.

Exemplary oxo acids of halogen atoms and their salts which can be employed include hypochlorous acid, chlorous acid, chloric acid, perchloric acid, hypobromous acid, bromic acid, perbromic acid, hypoiodous acid, iodous acid, iodic acid, orthoperiodic acid, methaperiodic acid and their salts. The cations of the salts which can be employed may be any cations such as an ammonium ion and various metallic ions, and preferred cations are alkali metal ions and alkaline earth metal ions.

Exemplary salts of the oxo acid of halogen atoms which can be employed include the hypochlorites such as sodium hypochlorite, potassium hypochlorite, calcium hypochlorite and barium hypochlorite; the chlorites such as sodium chlorite; the chlorates such as lithium chlorate, sodium chlorate, potassium chlorate, rubidium chlorate, cesium chlorate, magnesium chlorate and barium chlorate; the perchlorates such as aluminum perchlorate, calcium perchlorate, barium perchlorate, zinc perchlorate, cadmium perchlorate, mercury perchlorate, cerium perchlorate, lead perchlorate and ammonium perchlorate; the hypobromites such as sodium hypobromite and potassium hypobromite; the bromites such as sodium bromite; the bromates such as lithium bromate, sodium bromate, potassium bromate, rubidium bromate, cesium bromate, magnesium bromate, calcium bromate, strontium bromate, barium bromate, silver bromate, zinc bromate, cadmium bromate, mercury bromate, aluminum bromate, lanthanum bromate, samarium bromate, lead bromate and ammonium bromate; the perbromates such as potassium perbromate; the hypoiodites such as sodium hypoiodite, potassium hypoiodite, rubidium hypoiodite, cesium hypoiodite, calcium hypoiodite and barium hypoiodite; the iodates such as lithium iodate, sodium iodate, potassium iodate, potassium hydrogen iodate, rubidium iodate, cesium iodate, magnesium iodate, calcium iodate, strontium iodate, barium iodate, silver iodate, gold iodate, zinc iodate, cadmium iodate, mercury iodate, aluminum iodate, indium iodate, lanthanum iodate, cerium iodate, proseodium iodate, neodium iodate, gadrinium iodate, lead iodates and ammonium iodate; the periodates such as lithium periodate, sodium metaperiodate, dihydrogentrisodium orthoperiodate, trihydrogendisodium orthoperiodate, potassium metaperiodate, trihydrogendipotassium orthoperiodate, hydrogentripotassium dimesoperiodate, rubidium periodate, cesium periodate, barium periodate, silver metaperiodate, silver mesoperiodate, silver orthoperiodate, trihydrogensilver orthoperiodate, zinc periodate, cadmium periodate, lead periodate and ammonium periodate.

The complex compounds containing halogen ions may be either cationic or anionic halogen-containing complex compounds.

Exemplary complex compounds containing halogen ions include halogenic acid polyhalide salts such as ammonium dichlorobromate and tetramethylammonium tetrabromoiodate; metal acid halide salts such as potassium hexaiodotellurate, tetramethylammonium tetraiodomercurate, potassium tetraiodobismuthate, sodium tetrabromocuprate, cesium tetrabromoferrate, barium hexaiodostannate, potassium tetraiodoplumbate and potassium hexabromotellurate; complexes having ligands such as tetrabromo (diethylsuccinate)tin, octates(N,N-dimethylformamide)lanthanumtriiodide, hexakis(urea) chromiumtribromide, hexaamminechromiumtribromide, iodopentamminechromiumtribromide, tris(pyridine)molybdenumtriiodide, hexaamminecobalttribromide and bis(2,2'-bipyridine)copperdiiodide.

The organic halide which can be employed in this invention is represented by the formula:

$$R^6(X)_m$$

wherein
$R^6$ is an organic group having a valency of m;
X is a halogen atom and m is an integer of 1 or more.

When m is 2 or more, X may be two or more kinds of different halogen atoms. The halogen atom X may also be bonded to a hetero atom other than carbon such as nitrogen, phosphorus, oxygen, sulfur or selenium.

Exemplary organic halides which can be employed in this invention include aliphatic mono- and poly-halides such as methyl halides, ethyl halides, propyl halides(respective isomers), butyl halides(respective isomers), hexyl halides(respective isomers), octyl halides(respective isomers), perfluoroheptyl halides(respective isomers), vinyl halides, allyl halides, methylene halides, haloforms, tetrahalogenomethanes, alkylidene halides, ethane dihalides(respective isomers), ethane trihalides(respective isomers), ethane tetrahalides, butane dihalides(respective isomers), hexane dihalides(respective isomers), dihaloethylenes(respective isomers); and aromatic mono- and polyhalides such as halogenobenzenes, dihalogenobenzenes (respective isomers), trihalogenobenzenes(respective isomers), tetrahalogenobenzenes(respective isomers), hexahalogenobenzenes, halogenonaphthalenes, dihalogenonaphthalenes(respective isomers), halogenotoluenes(respective isomers), halogenoethylbenzenes(respective isomers), phenyliododichloride, iodosobenzene and iodoxybenzene; alicyclic halides such as cyclohexane halides and cyclobutane halides; arylaliphatic halides such as benzyl halides and phenethyl halides; heterocyclic halides such as furan halides, tetrahydrofuran halides, thiophene halides, imidazole halides and piperidine halides; acid halides such as acetyl halides and benzoyl halides; and N-halides such as N-halogenosuccinimides, N-halogenoalkylamines, N-halogenoacetamides and N-halogenobenzamides. Further, these organic groups may have various substituents such as a nitro group, a lower alkyl group, a cyano group, an alkoxy group, an aryloxy group, an aromatic group, a sulfoxide group, a sulfone group, a carbonyl group, an ester group and an amido group, and may also have an unsaturated group.

Exemplary halogen molecules which can be employed in this invention include chlorine molecule, bromine molecule and iodine molecule and halogeno intermolecules which consist of different halogen atoms such as chlorobromide, chloroiodide and bromoiodide.

The above described halogen-containing compounds may be used as a single species or two or more species as a mixture.

Of the halogen-containing compounds which can be used in this invention, those containing a bromine or iodine atom as the halogen atom are preferred, and those containing an iodine atom are more preferred.

The amount of the halogen-containing compound which can be employed is not particularly limited, and the amount of the halogen atom in the halogen-containing compound is typically about 0.001 to 10000 mols per platinum group metal atom of the platinum group metal or the compound containing at least one platinum group element employed as the main catalyst.

In the present invention a basic substance may be used as an additional promoter. However, when the halogen-containing compound is an alkali or alkaline earth metal halide, an onium halide, an oxo acid of a halogen atom or its salt, it is not always necessary to employ the basic substance as the additional promoter. On the other hand, when the halogen-containing compound is a complex compound containing a halogen ion, an organic halide or a halogen molecule, use of the basic substance increases the yield and the selectivity of a urethane compound produced and is accordingly preferred.

The basic substance which can be used, if desired or necessary, in this invention may be either inorganic or organic. Suitable examples of such basic substances include alkali metals such as lithium, sodium and potassium; alkaline earth metals such as magnesium, calcium and barium; alkali metal oxides such as sodium oxide, sodium peroxide, sodium hyperoxide, potassium oxide, potassium peroxide, dipotassium trioxide, potassium hyperoxide, rubidium oxide, rubidium peroxide, dirubidium trioxide, rubidium hyperoxide, rubidium ozonide, cesium oxide, cesium peroxide, dicesium trioxide, cesium hyperoxide and cesium ozonide; alkaline earth metal oxides such as beryllium oxide, magnesium oxide, calcium oxide, calcium peroxide, strontium oxide, strontium peroxide, barium oxide and barium peroxide; hydroxides of alkali metals or alkaline earth metals such as lithium hydroxide, sodium hydroxide, potassium hydroxide, rubidium hydroxide, cesium hydroxide, beryllium hydroxide, magnesium hydroxide, calcium hydroxide, strontium hydroxide and barium hydroxide; salts of a strong base and a weak acid such as sodium carbonate, sodium hydrogen carbonate, potassium carbonate, potassium hydrogen carbonate, barium carbonate, sodium silicate, magnesium silicate, potassium aluminate, calcium aluminate, sodium borate and barium borate; carbides such as calcium carbide and cesium carbide; hydroxides and oxides of aluminum group metals such as aluminum hydroxide, gallium hydroxide, indium hydroxide, thallium hydroxide and thallium oxide; oxides and hydroxides of rare earth metals such as lanthanum oxide, cerium oxide and cerium hydroxide; hydrides such as lithium hydride, sodium hydride, sodium borohydride, calcium hydride and lithium aluminum hydride; sulfides and hydrogen sulfides of alkali metals or alkaline earth metals such as sodium fulfide, sodium hydrogensulfide, potassium sulfide and calcium sulfide; quaternary ammonium hydroxides such as tetraethylammonium hydroxide and tetra-n-propylammonium hydroxide; quaternary phosphonium hydroxides such as methyltriphenylphosphonium hydroxide and tetramethylphosphonium hydroxide; tertiary sulfonium hydroxides such as triethylsulfonium hydroxide and triphenylsulfonium hydroxide; salts of a strong base and a weak organic acid such as sodium acetate, potassium benzoate, rubidium oxalate and barium propionate; alcoholates of alkali metals or alkaline earth metals such as sodium methylate, sodium ethylate and potassium ethylate; phenolates of alkali metals or alkaline earth metals such as sodium phenolate, potassium phenolate and magnesium phenolate; amides of alkali or alkaline earth metals such as lithium amide, sodium amide, calcium amide and lithium dimethylamide; tertiary amines and cyclic nitrogen-containing compounds having no N—H group such as trimethylamine, triethylamine, tri-n-butylamine, triphenylamine, diethylmethylamine, N,N-diethylaniline, N-methylpiperidine, N,N,-diethylpiperazine, N-methylmorpholine, triethylenediamine, hexamethylenetetramine, N,N,N',N'-tetramethylethylenediamine, dicyclohexylethylamine, 1,2,2,6,6-pentamethylpiperidine, pyridine, quinoline, phenanthroline, indole, N-methylimidazole, 1,8-diazabicyclo-(5,4,0)-undecene-7(DBU) and 1,5-diazabicyclo-(4,3,0)-nonene-5(DBN), etc.; crown compounds such as crown ethers, azacrown ethers, thiacrown ethers and azacrown; and complexes of these crown compounds with alkali metals or alkaline earth metals. Further, two or more groups exhibiting basicity may be present in the molecule also form part of a polymer such as anion exchange resins having a quaternary ammonium hydroxide group. Further, these basic substances or the groups having basicity may also be supported on or chemically bonded to a solid substance. These basic substances may be used either alone or as a mixture of two or more species.

The amount of the basic substance which can be employed is not particularly limited and is typically about 0.01 to about 1000 mols per halogen atom in the halogen-containing compound.

The amine with a replaceable hydrogen attached to the nitrogen which can be used as the starting material in this invention is a compound having at least one amino group represented by the following formulae in one molecule:

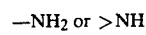

—NH$_2$ or >NH wherein the one line or the two lines bonded to a nitrogen atom indicate bonds between the nitrogen atom and other atoms or groups, such as a hydrogen atom, a halogen atom, an alkali metal, a hydroxyl group, an amino group, an aliphatic group, an alicyclic group, an aromatic group, an arylaliphatic group and a heterocyclic group.

In the secondary amines, the nitrogen atom may itself be an element forming a ring as in pyrrole, piperidine, piperazine and morpholine.

Exemplary primary amines which can be used include ammonia; aliphatic primary monoamines such as methylamine, ethylamine, propylamine(respective isomers), butylamine(respective isomers), pentylamine(respective isomers), hexylamine(respective isomers) and dodecylamine (respective isomers); aliphatic primary diamines such as ethylenediamine, diaminopropane(respective isomers), diaminobutane(respective isomers), diaminopentane(respective isomers); diaminohexane(respective isomers) and diaminodecane(respective isomers); aliphatic primary triamines such as 1,2,3-triaminopropane, triaminohexane(respective isomers), triaminononane(respective isomers) and triaminododecane(respective isomers); alicyclic primary mono- and poly-amines such as cyclopropylamine, cyclobutylamine, cyclopentylamine, cyclohexylamine, diaminocyclobutane, diaminocyclohexane(respective isomers) and triaminocyclohexane(respective isomers); arylaliphatic primary mono- and poly-amines such as benzylamine, di(aminomethyl)benzene(respective isomers), aminomethylpyridine (respective isomers), di(aminomethyl)pyridine (respective isomers), aminomethylnaphthalene(respective isomers) and di(aminomethyl)naphthalene(respective isomers); and heterocyclic primary amines such as aminofuran(respective isomers), aminotetrahydrofuran(respective isomers), aminothiophen(respective isomers), aminopyrrole(respective isomers), aminopyrrolidine(respective isomers); aromatic primary amines such as aniline, diaminobenzene(respective isomers), triaminobenzene(respective isomers), tetraaminobenzene(respective isomers), aminotoluene(respective isomers), diaminotoluene(respective isomers), aminopyridine(respective isomers), diaminopyridine(respective isomers), triaminopyridine(respective isomers), aminonaphthalene(respective isomers), diaminonaphthalene(respective isomers), triaminonaphthalene(respective isomers), tetraaminonaphthalene(respective isomers) and respective isomers of monoamines, diamines, triamines and tetraamines of diphenyl compounds represented by the formula:

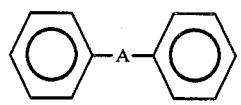

wherein A represents a chemical bond or a divalent group selected from the group consisting of —O—, —S—, —SO$_2$—, —CO— —CONH—, —COO—, —C(R$^7$)(R$^8$)— and —N(R$^7$)— wherein R$^7$ and R$^8$ each is a hydrogen atom, an aliphatic group or an alicyclic group.

In these aromatic primary amines, at least one hydrogen atom in the aromatic ring may be substituted with a substituent such as a halogen atom, a nitro group, a cyano group, an alkyl group, an alicyclic group, an aromatic group, an aralkyl group, an alkoxy group, a sulfoxide group, a sulfone group, a carbonyl group, an ester group and an amido group.

Of these aromatic amines, aniline, 2,4- and 2,6-diaminotoluene, chloroaniline(respective isomers), dichloroaniline(respective isomers), 4,4'- and 2,4'-diaminodiphenylmethane and 1,5-diaminonaphthalene are preferred.

Exemplary secondary amines which can be used in this invention include aliphatic secondary amines such as dimethylamine, diethylamine, dipropylamine(respective isomers), dibutylamine(respective isomers), dipentylamine (respective isomers), dihexylamine(respective isomers), ethylmethylamine, ethylpropylamine(respective isomers), butylmethylamine(respective isomers) and ethylhexylamine (respective isomers); alicyclic secondary amines such as dicyclopropylamine, dicyclohexylamine and methylcyclohexylamine; aromatic secondary amines such as N-methylaniline, N-ethylaniline, N-methyltoluidine(respective isomers), diphenylamine, N,N'-diphenylmethanediamine, N,N'-dimethylphenylenediamine(respective isomers), N-methylnaphthylamine(respective isomers) and dinaphthylamine(respective isomers); arylaliphatic secondary amines such as dibenzylamine, ethylbenzylamine and diphenethylamine; heterocyclic secondary amines such as difuranylamine and dithiophenylamine; and cyclic secondary amines such as pyrrolidine, pyrrole, 3-pyrrolidone, indole, carbazole, piperidine, piperazine, β-piperidone, γ-piperidone, imidazole, pyrazole, triazole, benzoimidazole, morpholine and 1,3-oxazine.

In these primary amines and secondary amines, one or more hydrogens of the organic group bonded to the nitrogen may be substituted by a substituent such as a lower aliphatic group, an amino group, a carboxyl group, an ester group, an alkoxy group, a cyano group, a halogen atom, a nitro group, a urethane group, a sulfoxide group, a sulfone group, a carbonyl group, an amide, an aromatic group and arylaliphatic group. Further, these primary amines and secondary amines may also have an unsaturated bond.

In this invention it is also possible to use compounds having an amino group and a hydroxyl group in the molecule such as ethanolamine, propanolamine and o-aminobenzyl alcohol. In such a case, cyclic urethanes can be produced.

In order to produce urethane compounds to be employed as starting materials for the preparation of isocyanate compounds, it is preferred that the primary amines are used.

The urea compound which can be employed as the starting material in this invention is a compound having at least one urea bond represented by the following formula in one molecule:

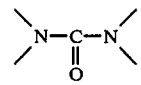

wherein the two lines bonded to a nitrogen atom indicate bonds between the nitrogen atom and other atoms or groups such as a hydrogen atom, a halogen atom, an aliphatic group, an alicyclic group, an aromatic group, an arylaliphatic group and a heterocyclic group, and the nitrogen atom or the urea bond by itself may be an element forming a ring.

Suitable examples of such urea compounds which can be employed in this invention include non-substituted urea, i.e., urea and mono-, di-, tri- or tetra-substituted ureas.

Exemplary mono-substituted ureas include aliphatic mono-substituted ureas such as methylurea, ethylurea, propylurea(respective isomers), butylurea(respective isomers) and hexylurea(respective isomers); alicyclic mono-substituted ureas such as cyclopropylurea, cyclobutylurea and cyclohexylurea; arylaliphatic mono-substituted ureas such as benzylurea and β-phenethylurea; heterocyclic mono-substituted ureas such as furanylurea and thiophenylurea; aromatic mono-substituted ureas such as phenylurea, tolylureas and naphthylureas.

Exemplary di-substituted ureas include aliphatic N,N-di-substituted ureas such as N,N-dimethylurea, N,N-diethylurea, N,N-di-n-propylurea, N,N-di-n-butylurea, N,N-di-n-hexylurea, N-ethyl-N-methylurea and N-ethyl-N-n-butylurea; alicyclic N,N-di-substituted ureas such as N,N-dicyclopropylurea, N,N-dicyclobutylurea, N,N-dicyclohexylurea, N-cyclopropyl-N-methylurea and N-cyclohexyl-N-ethylurea; arylaliphatic N,N-di-substituted ureas such as N,N-dibenzylurea and N-benzyl-N-methylurea; heterocyclic N,N-di-substituted ureas such as N,N-difuranylurea, N,N-dithiophenylurea and N-furanyl-N-methylurea; aromatic N,N-di-substituted ureas such as N,N-diphenylurea, N,N-p-tolylurea, N,N-o-tolylurea, N,N-m-tolylurea, N,N-di-α-naphthylurea, N,N-di-β-naphthylurea, N-phenyl-N-methylurea, N-phenyl-N-p-tolylurea, N-β-naphthyl-N-benzylurea and N-phenyl-N-cyclohexylurea; aliphatic N,N'-di-substituted ureas such as N,N'-dimethylurea, N,N'-diethylurea, N,N'-di-n-propylurea, N,N'-di-n-butylurea, N,N'-di-n-hexylurea, N-ethyl-N'-methylurea, N-ethyl-N'-n-butylurea and N-n-hexyl-N'-methylurea; alicyclic N,N'-di-substituted ureas such as N,N'-dicyclopropylurea, N,N'-dicyclobutylurea, N,N'-dicyclohexylurea, N-cyclopropyl-N'-methylurea and N-cyclohexyl-N'-ethylurea; arylaliphatic N,N'-di-substituted ureas such as N,N'-dibenzylurea and N-benzyl-N'-methylurea; heterocyclic N,N'-di-substituted ureas such as N,N'-difuranylurea and N,N'-dithiophenylurea; aromatic N,N'-di-substituted ureas such as N,N'-diphenylurea, N,N'-di-p-tolylurea, N,N'-di-o-tolylurea, N,N'-di-m-tolylurea, N,N'-di-α-naphthylurea, N,N'-di-β-naphthylurea, N-phenyl-N'-p-tolylurea, N-phenyl-N'-α-naphthylurea, N-phenyl-N'-ethylurea, N-α-naphthyl-N'-benzylurea and N-phenyl-N'-cyclohexylurea; and ureas of cyclic nitrogen-containing compounds such as piperidylurea and pyrrolidinylurea.

Exemplary tri-substituted ureas include aliphatic tri-substituted ureas such as trimethylurea, triethylurea, tri-n-propylurea, tri-n-butylurea, tri-n-hexylurea, N,N-dimethyl-N,-ethylurea, N,N-diethyl-N'-n-butylurea and N-methyl-N-ethyl-N'-n-butylurea; alicyclic tri-substituted ureas such as tricyclopropylurea, tricyclohexylurea, N,N'-dicyclohexyl-N'-methylurea, N-cyclohexyl-N'-methylurea, N-cyclohexyl-N-ethyl-N'-n-butylurea and N,N-diethyl-N'-cyclobutylurea; heterocyclic tri-substituted ureas such as trifuranylurea, trithiophenylurea and N,N'-difuranyl-N-methylurea; aromatic tri-substituted ureas such as triphenylurea, tri-p-tolylurea, tri-o-tolylurea, tri-m-tolylurea, tri-α-naphthylurea, tri-β-naphthylurea, N,N-diphenyl-N'-methylurea, N,N'-diphenyl-N'-methylurea, N, N'-diphenyl-N-cyclohexylurea, N,N-dimethyl-N'-phenylurea, N-phenyl-N-ethyl-N'-benzylurea; and ureas of N-substituted cyclic nitrogen-containing compounds such as N-ethylpiperidylurea and N-methylpyrrodinylurea.

Exemplary tetra-substituted ureas include aliphatic tetra-substituted ureas such as tetramethylurea, tetraethylurea, tetra-n-propylurea, tetra-n-hexylurea, diethyldimethylurea and ethyltrimethylurea; alicyclic tetra-substituted ureas such as tetracyclopropylurea, tetracyclohexylurea, dicyclohexyldiethylurea and cyclobutyltrimethylurea; arylaliphatic tetra-substituted ureas such as tetrabenzylurea, tribenzylmethylurea, dibenzyldiethylurea and benzyltrimethylurea; heterocyclic tetrasubstituted ureas such as tetrafuranylurea, tetrathiophenylurea and furanyltrimethylurea; aromatic tetrasubstituted ureas such as tetraphenylurea, tetra-p-tolylurea, tetra-m-tolylurea, tetra-o-tolylurea, tetra-α-naphthylurea, tetra-β-naphthylurea, methyltriphenylurea, diethyldiphenylurea, dicyclohexyldiphenylurea, α-naphthyltriethylurea and β-naphthyltriethylurea; cyclic ureas in which a urea bond is the member constituting a ring such as 2-imidazolone, 2-imidazolidone, biotin, hydantoin, N, N'-hexamethylurea, parabanic acid and benzimidazole; compounds having at least two urea bonds in the molecule such as N,N'-dimethylcarbamoylhexamethylenediamine and N,N'-diphenylcarbamoylhexamethylenediamine; and polymeric ureas having units of the following formula in the molecule:

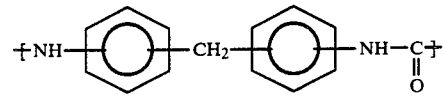

In these substituted urea compounds at least one hydrogen in the substituent may be substituted with a lower aliphatic group, an amino group, a carboxyl group, an ester group, an alkoxy group, a cyano group, a halogen atom, a nitro group, a urethane group, a sulfoxide group, a sulfone group, a carbonyl group, an amido group, an aromatic group or arylaliphatic group.

In preparing urethane compounds useful as the starting material for isocyanate compounds it is preferred that N,N'-di-substituted ureas are employed. In order to readily obtain N-monoaromatic urethane compounds, N,N'-diarylureas are preferably employed.

As is apparent from the above, any of a wide variety of urea compounds may be utilized in this invention. In carrying out the urethanation of a primary or secondary amine, the counterpart urea compound may sometimes be present as an intermediate in the reaction system but this urea compound is finally urethanated.

According to this invention, the primary amine, the secondary amine and the urea compound may be singly or in various mixtures.

The organic hydroxyl compounds which can be used in this invention are aliphatic and aromatic compounds such as monohydric or polyhydric alcohols or monohydric or polyhydric phenols. Such alcohols include $C_{1-20}$ straight or branched monohydric or polyhydric alkanols or alkenols and $C_{3-20}$ monohydric or polyhydric cycloalkanols or cycloalkenols and $C_{7-20}$ monohydric or polyhydric aralkylalcohols. Further, these alcohols may also have a substituent such as a halogen atom, a cyano group, an alkoxy group, a sulfoxide group, a sulfone group, a carbonyl group, an ester group and an amide group.

Exemplary alcohols include aliphatic alcohols such as methanol, ethanol, propanol(respective isomers), butanol(respective isomers), pentanol(respective isomers), hexanol(respective isomers), heptanol(respective isomers), octanol(respective isomers), nonyl alcohol(respective isomers), decyl alcohol(respective isomers), undecyl alcohol(respective isomers), lauryl alcohol(respective isomers), tridecyl alcohol(respective isomers), tetradecyl alcohol(respective isomers) and pentadecyl alcohol(respective isomers); cycloalkanols such as cyclohexanol and cycloheptanol; alkylene glycol monoethers such as ethylene glycol monomethylether, ethylene glycol monoethylether, diethylene glycol monomethylether, diethylene glycol monoethylether, triethylene glycol monomethylether, triethylene glycol monoethylether, propylene glycol monomethylether and propylene glycol monoethylether; polyhydric alcohols such as ethylene glycol, propylene glycol, diethylene glycol, dipropylene glycol, glycerine, hexanetriol and trimethylolpropane; and aralkyl alcohols such as benzyl alcohol.

Exemplary phenols include phenol, various alkylphenols, various alkoxyphenols, various halogenated phenols, dihydroxybenzene, 4,4'-dihydroxydiphenylmethane, bisphenol-A and hydroxynaphthalene.

Of the above described organic hydroxyl compounds, $C_{1-10}$ aliphatic monoalcohols, $C_{3-10}$ alicyclic or $C_{7-15}$ aralkyl monoalcohols are preferred.

In the case of the urethanation of a primary or secondary amine, the amount of the alcohol or phenol employed is typically at least one mol per amino group of the primary or secondary amine. In the case of the urethanation of a urea compound, the amount of the alcohol or phenol employed is at least two mols per urea group of the urea compound. In both cases it is preferred that the alcohol or phenol is employed as a reaction medium. In such a case the amount of the alcohol or phenol is typically about 3 to 100 mols per amino group of the primary or secondary amine or per urea group of the urea compound.

The carbon monoxide which can be employed as one starting material in this invention may be pure carbon monoxide or may contain other gases such as nitrogen, argon, helium, carbon dioxide, a hydrocarbon or a halogenated hydrocarbon. A small amount, i.e., less than about 10% by mol of hydrogen based on carbon monoxide does not affect adversely the urethanation using the catalyst system of this invention, and accordingly in this invention carbon monoxide containing such a small amount of hydrogen may be advantageously employed from the industrial viewpoint.

The amount of carbon monoxide which can be employed is typically at least one mol, preferably about 2 to about 100 mols per amino group of the primary or secondary amine or per urea group of the urea compound.

The oxidizing agent which can be used in this invention may be molecular oxygen or an organic nitro compound or a mixture thereof. Molecular oxygen is preferred. The molecular oxygen means pure oxygen or a gas containing oxygen such as air. The molecular oxygen may also be diluted by the addition of other gases not interfering with the reaction to air or pure oxygen including inert gases such as nitrogen, argon, helium and carbon dioxide. In some cases the molecular oxygen may also contain a gas such as hydrogen, carbon monoxide, a hydrocarbon and a halogenated hydrocarbon.

The organic nitro compound which can be used in this invention may be either an alicyclic, aliphatic or aromatic nitro compound. Exemplary alicyclic nitro compounds include nitrocyclobutane, nitrocyclopentane, nitrocyclohexane, dinitrocyclohexane(respective isomers) and bis-(nitrocyclohexyl) methane. Exemplary aliphatic nitro compounds include nitromethane, nitroethane, nitropropane (respective isomers), nitrobutane(respective isomers), nitropentane(respective isomers), nitrohexane(respective isomers), nitrodecane(respective isomers), 1,2-dinitroethane, dinitropropane(respective isomers), dinitrobutane (respective isomers), dinitropentane(respective isomers), dinitrohexane(respective isomers), dinitrodecane(respective isomers), phenylnitromethane, bis-(nitromethyl) cyclohexane and bis-(nitromethyl)benzene. Exemplary aromatic nitro compounds include nitrobenzene, dinitrobenzene(respective isomers), nitrotoluene(respective isomers), dinitrotoluene(respective isomers), nitropyridine(respective isomers), dinitropyridine(respective isomers), nitronaphthalene(respective isomers), dinitronaphthalene(respective isomers), and respective isomers of mononitro compounds and di-nitro compounds of the diphenyl compounds represented by the formula

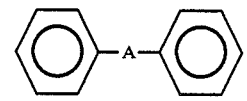

wherein A is the same as defined above.

In these nitro compounds, at least one hydrogen may be substituted by a substituent such as a halogen atom, an amino group, a cyano group, an alkyl group, an aliphatic group, an aromatic group, an aralkyl group, an alkoxy group, a sulfoxide group, a sulfone group, a carbonyl group, an ester group, an amido group.

When molecular oxygen is used as the oxidizing agent in the present invention, the urethanation of, for example, a primary amine proceeds according to the general reaction equation as follows:

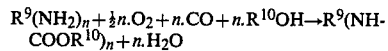

wherein $R^9$ and $R^{10}$ each represents an organic group and n represents the number of amino groups in one molecule of an amino compound.

In the case of a secondary amine the urethanation proceeds substantially in the same way as described above.

The urethanation of a urea compound proceeds according to the general reaction equation as follows:

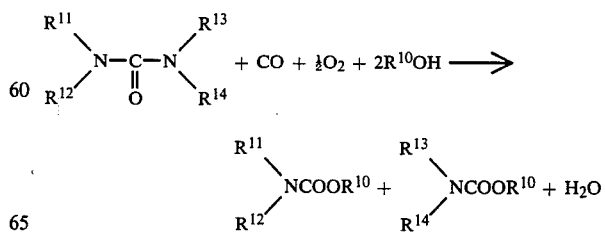

wherein $R^{11}$, $R^{12}$, $R^{13}$ and $R^{14}$ each represents a hydrogen atom, an aliphatic group, an alicyclic group, an arylaliphatic group, a heterocyclic group or an aromatic group and $R^{10}$ represents an organic group.

The molecular oxygen may be less or more than its equivalent amount, but a mixture of oxygen and carbon monoxide or a mixture of oxygen and an organic hydroxyl compound should be used in the range outside the explosion limit.

When an organic nitro compound is used as the oxidizing agent, the organic nitro compound also participates in the reaction to form a urethane compound. Accordingly, when the structure of the organic group in the organic nitro compound is different from that in the primary or secondary amine or the substituent in the urea compound, different kinds of urethane compounds are obtained corresponding to the respective structures. When both have the same structure, the same urethane compound is obtained. In this case, the urethanation of, for example, a primary amine proceeds according to the following reaction equation:

$$2R^9(NH_2)_n + R^{15}(NO_2)_n + 3n.CO + 3n.R^{10}OH \rightarrow 2R^9(NHCOOR^{10})_n + R^{15}(NHCOOR^{10})_n + 2n.H_2O$$

wherein $R^9$, $R^{10}$, and n are the same as defined above, and $R^{15}$ represents a residue of an organic nitro compound other than the nitro group and for simplicity the number of nitro groups in the organic nitro compound is assumed to be the same as that of amino groups in the primary amine.

In the case of the urethanation of a urea compound with, for example, an organic mononitro compound, the reaction proceeds as follows:

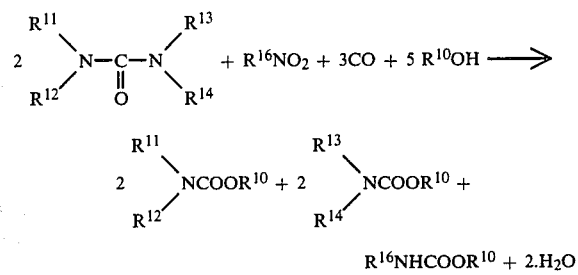

wherein $R^{10}$, $R^{11}$, $R^{12}$, $R^{13}$ and $R^{14}$ are the same as defined above, and $R^{16}$ represents an organic residue of an organic nitro compound.

When only an organic nitro compound is used as the oxidizing agent, the amount of the primary amine, secondary amine or urea compound to the organic nitro compound may preferably be one mol of the nitro group per 2 mols of the amino group or the urea group. It is possible to practice the invention at a ratio apart from the stoichiometric ratio but it is advantageous to adopt an equivalent ratio of the amino group or urea group to the nitro group of 1.1:1 to 4:1, preferably 1.5:1 to 2.5:1.

When molecular oxygen or other oxidizing agents are employed at the same time, the organic nitro compound may be used in an amount less than the stoichiometric amount.

In the process of this invention, it is preferred to use an excess of an organic hydroxyl compound as the reaction medium. If necessary, other solvents which do not affect the reaction adversely may also be used. Exemplary solvents which can be employed include aromatic hydrocarbons such as benzene, toluene, xylene and mesitylene; nitriles such as acetonitrile and benzonitrile; sulfones such as sulforane, methylsulforane and dimethylsulforane; ethers such as tetrahydrofuran, 1,4-dioxane and 1,2-dimethoxyethane; ketones such as acetone, methyl ethyl ketone; esters such as ethyl acetate and ethyl benzoate; and amides such as N,N-dimethylformamide, N,N-dimethylacetamide, N-methylpyrrolidone and hexamethylphosphoramide.

Further, it is also possible to use, as a solvent, a halogenated aromatic hydrocarbon which is one kind of the organic halide to be used as the promoter in this invention such as chlorobenzene, dichlorobenzene, trichlorobenzene, fluorobenzene, chlorotoluene, chloronaphthalene and bromonaphthalene; a halogenated aliphatic hydrocarbon or a halogenated alicyclic hydrocarbon such as chlorohexane, chlorocyclohexane, trichlorotrifluoroethene, methylene chloride and carbon tetrachloride.

The reaction according to this invention can hardly be affected adversely by the presence of a small amount of water. However, the presence of water might cause some side reactions such as the hydrolysis of urethane compounds and the water gas reaction of carbon monoxide and accordingly, it is possible to employ additives having a dehydrating action. Suitable examples of such additives include zeolites, orthoesters, ketals, acetals, enolethers and trialkyl orthoborates.

In the process of this invention, the reaction is carried out at a temperature of from about 80° C. to about 300° C., preferably from 120° to 220° C. The reaction pressure is typically in the range of from about 1 Kg/cm² to about 500 Kg/cm², preferably from about 20 Kg/cm² to about 300 Kg/cm². The reaction time which may vary depending on the reaction system employed and other reaction conditions chosen is typically about one minute to about 10 hours.

The reaction of this invention can be carried out either batch-wise or continuously by removing continuously the reaction mixture from the reaction system while continuously feeding the reactants into the reaction system.

A further understanding of the present invention, and the advantages thereof, can be had by reference to the following examples.

The conversion of a primary or secondary amine, a urea compound, an organic nitro compound or molecular oxygen, the yield of a urethane compound, the selectivity of an urethane compound and the selectivity of molecular oxygen to the urethanation reaction were determined in the examples according to the following formulae:

Conversion of A (%) =

$$\frac{(\text{Mol of } A \text{ supplied}) - (\text{Mol of remaining } A)}{\text{Mol of } A \text{ supplied}} \times 100$$

or $$= \frac{\text{Mol of reacted } A}{\text{Mol of } A \text{ supplied}} \times 100$$

wherein A is a primary or secondary amine, a urea compound, an organic nitro compound or molecular oxygen.

Yield of a urethane compound (%) =

$$\frac{\text{Mol of a urethane compound formed}}{\text{Mol of a primary or secondary amine supplied}} \times 100$$

-continued or $$= \frac{\text{Mol of a urethane compound formed}}{\text{Mol of a urea compound supplied}} \times \frac{1}{2} \times 100$$

in case of a syn-urea compound employed as the starting material.

Selectivity of a urethane compound (%) =

$$\frac{\text{Yield of a urethane compound (\%)}}{\text{Conversion of a primary or secondary amine or a urea compound (\%)}} \times 100$$

Selectivity of molecular oxygen to the urethanation reaction (%) =

$$\frac{\text{Yield of a urethane compound (\%)}}{\text{Conversion of molecular oxygen (\%)}} \times 100$$

The autoclave employed in the following examples were internally lined with titanium or made of Hastelloy-C.®

EXAMPLE 1

In a 140 ml stirring type autoclave were charged 40 mmols of aniline, 40 ml of ethanol, 0.5 mg-atom of palladium black and 5 mmols of cesium iodide. After the air inside the autoclave had been replaced with carbon monoxide, carbon monoxide was pressurized into the autoclave to 80 Kg/cm² and then oxygen was pressurized into the autoclave to 6 Kg/cm², resulting in a total pressure of 86 Kg/cm². The reaction was carried out at 160° C. for one hour with stirring, and subsequently the reaction mixture obtained was subjected to filtration. As the result of analysis of the filtrate, the conversion of aniline was 87% and the yield of ethyl N-phenylcarbamate was 85% with a selectivity of 98%. In the filtrate palladium was not detected.

EXAMPLE 2

The procedure of Example 1 was repeated except that 5 mmols of tetramethylammonium iodide were employed instead of the cesium iodide. The filtrate obtained was a yellowish solution. As a result, the conversion of aniline was 81% and the yield of ethyl N-phenylcarbamate was 80% with a selectivity of 99%. In the filtrate palladium was not detected. When ethanol was distilled from this solution under reduced pressure and then tetramethylammonium iodide was removed by washing with water, 5.3 g of yellow crystals were precipitated. The crude crystals thus obtained were ethyl N-phenylcarbamate of 99% purity and recrystallized once from ethanol to give white crystals of ethyl N-phenylcarbamate of 100% purity.

EXAMPLE 3

An anion exchange resin (Amberlyst® A-26, OH-form) having units of the formula:

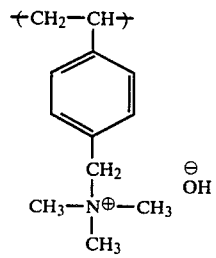

was treated with hydroiodic acid to exchange the hydroxyl groups with iodine anions and then dried at 100° C. under reduced pressure. One gram of the iodine-containing anion exchange resin, 40 mmols of aniline, 40 ml of ethanol and 0.5 mg-atom of palladium black were charged into a 140 ml stirring type autoclave. After the air inside the autoclave was replaced with carbon monoxide, carbon monoxide was pressurized into the autoclave to 80 Kg/cm², and subsequently oxygen was pressurized into the autoclave to 6 Kg/cm², resulting in a total pressure of 86 Kg/cm². The reaction was carried out with stirring at 150° C. for one hour, and then the reaction mixture was subjected to filtration. As the result of analysis of the filtrate, the conversion of aniline was 83% and the yield of ethyl N-phenylcarbamate was 81% with a selectivity of 98%.

When the above described procedure was repeated by using the palladium black and the anion exchange resin separated by filtration as such, the result obtained was as good as the above, i.e., the conversion of aniline was 82% and the yield of ethyl N-phenylcarbamate was 80% with a selectivity of 98%.

The reaction solution obtained in either case was yellowish and when the reaction solution was distilled under reduced pressure, yellow crystals were precipitated. The crude crystals thus obtained were ethyl N-phenylcarbamate of 99% purity and recrystallized once from ethanol to give white crystals of a high purity.

EXAMPLE 4

The procedure of Example 1 was repeated except that 1 mmol of potassium metaperiodate was employed instead of the cesium iodide. As a result, the conversion of aniline was 89% and the yield of ethyl N-phenylcarbamate was 85% with a selectivity of 96%.

EXAMPLE 5

The procedure of Example 1 was repeated except that 0.25 mmol of potassium tetraiodobismuthate was employed instead of the cesium iodide. As a result, the conversion of aniline was 81% and the yield of ethyl N-phenylcarbamate was 70% with a selectivity of 86%.

EXAMPLE 6

The procedure of Example 1 was repeated except that 0.3 mmol of iodoform and 1 mmol of rubidium hydroxide were employed instead of the cesium iodide. As a result, the conversion of aniline was 85% and the yield of ethyl N-phenylcarbamate was 82% with a selectivity of 97%. In the filtrate obtained no palladium was detected. The selectivity of the oxygen reacted to the urethanation was 93%.

When the above described procedure was repeated except that the rubidium was not employed, the conversion of aniline ws 45% and the yield of ethyl N-phenylcarbamate was 41% with a selectivity of 91%, and the selectivity of the oxygen to the urethanation was 70%.

The reaction solution obtained in either case was transparent and yellowish.

It is clear from this example that a urethane compound can be obtained at a high selectivity using only an organic halide and palladium, and the yield and the selectivity can be remarkably increased by additional use of a basic substance.

EXAMPLE 7

The procedure of Example 1 was repeated except that 1 mmol of iodine and 1 mmol of triethylamine were employed instead of the cesium iodide. As a result, the conversion of aniline was 90% and the yield of ethyl N-phenylcarbamate was 86% with a selectivity of 96%. In the filtrate no palladium was detected.

When the above described procedure was repeated except that the triethylamine was not employed, the conversion of aniline was 42% and the yield of ethyl N-phenylcarbamate was 28% with a selectivity of 67%.

COMPARATIVE EXAMPLE 1

The procedure of Example 1 was repeated except that the cesium iodide was not employed. As a result, the conversion of aniline was 8% and the yield of ethyl N-phenylcarbamate was only 1.9%.

COMPARATIVE EXAMPLE 2

The procedure of Example 1 was repeated except that 1 mmol of triethylamine was employed instead of the cesium iodide. As a result, the conversion of aniline was 3% and the yield of ethyl N-phenylcarbamate was only 1%

EXAMPLES 8 TO 119

The procedure of Example 1 was repeated except that 0.5 mg-atom of a platinum group metal or a compound containing the platinum group element based on the metal element set forth in Table 1 was employed in the presence or absence of a basic substance set forth in Table 1 instead of the cesium iodide.

The results are shown in Table 1.

TABLE 1

| Example No. | Pt Group Metal or Compound Containing At Least One Pt Group Element*[1] | Halogen-containing Compound | (mmol) | Basic Substance | (mmol) | Ph-NH₂ Conversion (%) | Ph-NHCOOC₂H₅ Yield (%) | Selectivity (%) |
|---|---|---|---|---|---|---|---|---|
| 8 | Pd Black | LiCl | 5 | — | | 55 | 34 | 62 |
| 9 | " | " | 3 | RbOH | 1 | 76 | 53 | 70 |
| 10 | " | MgCl₂ | 5 | — | | 71 | 50 | 70 |
| 11 | " | KBr | 5 | — | | 76 | 56 | 74 |
| 12 | " | " | 3 | RbOH | 1 | 82 | 66 | 80 |
| 13 | " | CsBr | 5 | — | | 77 | 62 | 81 |
| 14 | " | BaBr₂ | 5 | — | | 50 | 39 | 78 |
| 15 | " | LiI | 5 | — | | 70 | 56 | 80 |
| 16 | " | NaI | 5 | — | | 69 | 62 | 90 |
| 17 | " | KI | 5 | — | | 79 | 72 | 91 |
| 18 | " | RbI | 5 | — | | 81 | 78 | 96 |
| 19 | " | MgI₂ | 5 | — | | 65 | 50 | 77 |
| 20 | " | SrI₂.3H₂O | 5 | — | | 45 | 32 | 71 |
| 21 | " | BaI₂.2H₂O | 5 | — | | 47 | 38 | 81 |
| 22 | " | " | 0.5 | KOH | 1 | 80 | 74 | 93 |
| 23 | 5% Pd/C | CsI | 5 | — | | 83 | 75 | 90 |
| 24 | 5% (Pd—Te)/C*[2] | CsI | 5 | — | | 88 | 81 | 92 |
| 25 | Lindlar Catalyst*[3] | " | 5 | — | | 80 | 70 | 88 |
| 26 | 5% Pd/Al₂O₃ | " | 5 | — | | 85 | 79 | 93 |
| 27 | 5% Rh/C | " | 5 | — | | 75 | 66 | 88 |
| 28 | RhI₃ | " | 5 | — | | 80 | 66 | 83 |
| 29 | Ru Black | " | 5 | — | | 52 | 44 | 85 |
| 30 | IrCl₃ | " | 5 | — | | 53 | 34 | 65 |
| 31 | Pd Black | NH₄Cl | 5 | — | | 70 | 51 | 73 |
| 32 | " | Ph-NH₂.HCl | 5 | — | | 73 | 53 | 73 |
| 33 | " | NH₄Br | 5 | — | | 77 | 63 | 82 |
| 34 | " | pyridine.HBr | 5 | — | | 70 | 55 | 79 |
| 35 | " | NH₄I | 5 | — | | 85 | 79 | 93 |
| 36 | " | (C₂H₅)₃N.HI | 5 | — | | 80 | 76 | 95 |
| 37 | " | HI | 5 | pyridine | 5 | 88 | 82 | 93 |

TABLE 1-continued

| Example No. | Pt Group Metal or Compound Containing At Least One Pt Group Element*1 | Halogen-containing Compound (mmol) | | Basic Substance (mmol) | | ⌬—NH₂ Conversion (%) | ⌬—NHCOOC₂H₅ Yield (%) | Selectivity (%) |
|---|---|---|---|---|---|---|---|---|
| 38 | " | [(CH₃)₃N—⌬]⊕I⊖ | 5 | — | | 85 | 82 | 97 |
| 39 | " | [(CH₃)₄N]⊕I⊖ | 1 | (C₂H₅)₃N | 1 | 87 | 85 | 98 |
| 40 | 5% Pd/C | [(CH₃)₄N]⊕I⊖ | 5 | — | | 85 | 83 | 98 |
| 41 | 5% (Pd—Te)/C*2 | " | 5 | — | | 83 | 80 | 96 |
| 42 | 5% Pd/Al₂O₃ | " | 5 | — | | 88 | 86 | 98 |
| 43 | Lindlar Catalyst*3 | " | 5 | — | | 75 | 69 | 92 |
| 44 | 5% Ph/C | " | 5 | — | | 77 | 69 | 90 |
| 45 | RhI₃ | " | 5 | — | | 79 | 67 | 85 |
| 46 | 5% Pt/C | [(CH₃)₄N]⊕I⊖ | 5 | — | | 53 | 40 | 75 |
| 47 | Pd Black | [(C₆H₅)₄P]⊕Br⊖ | 5 | — | | 75 | 66 | 88 |
| 48 | " | [(C₆H₅)₃PCH₃]⊕I⊖ | 5 | (C₂H₅)₃N | 1 | 85 | 82 | 96 |
| 49 | " | [(CH₃)₃S]⊕I⊖ | 5 | — | | 40 | 28 | 70 |
| 50 | " | " | 2 | (n-C₄H₉)₃N | 1 | 75 | 66 | 88 |
| 51 | " | [(C₆H₅)₃AsCH₃]⊕I⊖ | 5 | — | | 78 | 72 | 92 |
| 52 | " | " | 2 | NaHCO₃ | 1 | 84 | 79 | 94 |
| 53 | 5% Rh/C | [(C₆H₅)PCH₃]⊕I⊖ | 5 | — | | 73 | 59 | 81 |
| 54 | RhI₃ | " | 5 | — | | 75 | 60 | 80 |
| 55 | Ru Black | " | 5 | — | | 55 | 45 | 82 |
| 56 | Pd Black | KH(IO₃)₂ | 1 | — | | 52 | 48 | 93 |
| 57 | " | " | 1 | K₂CO₃ | 1 | 80 | 75 | 94 |
| 58 | " | KBrO₃ | 1 | — | | 50 | 42 | 84 |
| 59 | " | " | 1 | DBU*5 | 1 | 70 | 63 | 90 |
| 60 | " | HIO₃ | 1 | — | | 60 | 54 | 90 |
| 61 | " | " | 0.8 | CsOH | 1 | 82 | 75 | 92 |
| 62 | " | KIO₄ | 1 | (C₂H₅)₃N | 1 | 90 | 87 | 97 |
| 63 | " | CsIO₄ | 1 | — | | 90 | 86 | 96 |
| 64 | 5% Pd/C | KIO₄ | 1 | — | | 88 | 83 | 94 |
| 65 | 5% Rh/C | " | 1 | — | | 78 | 69 | 89 |
| 66 | Ru Black | " | 1 | — | | 60 | 50 | 83 |
| 67 | 5% Pt/C | " | 1 | — | | 58 | 45 | 78 |
| 68 | Pd Black | [(CH₃)₄N][I₅] | 0.2 | — | | 48 | 35 | 73 |
| 69 | " | " | 0.2 | RbOH | 1 | 78 | 72 | 92 |
| 70 | " | K[PbI₃]·2H₂O | 0.4 | — | | 60 | 53 | 88 |
| 71 | " | " | 0.3 | RbOH | 1 | 80 | 72 | 90 |
| 72 | Pd Black | K₂[TeBr₆] | 0.2 | — | | 78 | 66 | 85 |
| 73 | " | " | 0.2 | Na₂B₄O₇·10H₂O | 1 | 85 | 80 | 90 |
| 74 | " | K[BiI₄]·H₂O | 0.3 | (n-C₃H₇)₄NOH | 1 | 87 | 82 | 94 |
| 75 | " | K₂[HgI₄]·2H₂O | 0.3 | — | | 66 | 59 | 90 |
| 76 | 5% Rh/C | K₂[TeBr₆] | 0.4 | — | | 70 | 57 | 81 |
| 77 | RhI₃ | K[BiI₄]·H₂O | 0.3 | — | | 73 | 60 | 82 |
| 78 | Pd Black | ⌬—CH₂Cl | 1 | — | | 32 | 24 | 75 |
| 79 | " | (CO)₂NBr*4 | 1 | — | | 38 | 32 | 84 |
| 80 | " | CH₃I | 1 | — | | 40 | 36 | 90 |
| 81 | " | " | 0.8 | (C₂H₅)₃N | 1 | 88 | 84 | 95 |
| 82 | " | CI₄ | 0.25 | — | | 50 | 47 | 94 |
| 83 | " | " | 0.2 | C₂H₅ONa | 1 | 88 | 83 | 94 |
| 84 | " | CF₃(CF)₆I | 1 | — | | 50 | 45 | 90 |
| 85 | Pd Black | ⌬—I | 1 | — | | 48 | 42 | 88 |
| 86 | 5% Rh/C | CHI₃ | 0.3 | — | | 42 | 38 | 90 |
| 87 | " | " | 0.3 | RbOH | 1 | 78 | 70 | 90 |
| 88 | RhI₃ | CHI₃ | 0.3 | — | | 51 | 45 | 89 |
| 89 | " | CHI₃ | 0.3 | RbOH | 1 | 78 | 70 | 90 |

TABLE 1-continued

| Example No. | Pt Group Metal or Compound Containing At Least One Pt Group Element*1 | Halogen-containing Compound (mmol) | | Basic Substance (mmol) | | ⌬—NH₂ Conversion (%) | ⌬—NHCOOC₂H₅ Yield (%) | Selectivity (%) |
|---|---|---|---|---|---|---|---|---|
| 90 | Ru Black | " | 0.3 | — | | 40 | 30 | 75 |
| 91 | " | " | 0.3 | RbOH | 1 | 73 | 62 | 85 |
| 92 | IrCl₃ | " | 0.3 | — | | 35 | 25 | 71 |
| 93 | " | " | 0.3 | RbOH | 1 | 58 | 46 | 80 |
| 94 | 5% Pt/C | " | 0.3 | RbOH | 1 | 70 | 57 | 82 |
| 95 | Pd Black | Br₂ | 1 | — | | 38 | 21 | 55 |
| 96 | " | " | 1 | RbOH | 1 | 68 | 60 | 88 |
| 97 | " | I₂ | 1 | NaOH | 1 | 92 | 87 | 95 |
| 98 | " | " | 1 | CsOH | 1 | 90 | 86 | 96 |
| 99 | " | " | 1 | Ba(OH)₂·8H₂O | 1 | 75 | 69 | 92 |
| 100 | " | " | 1 | CaO | 1 | 70 | 62 | 89 |
| 101 | " | " | 1 | BaO | 1 | 76 | 71 | 93 |
| 102 | " | " | 1 | 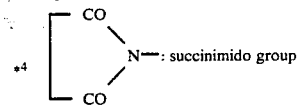 | 1 | 92 | 89 | 97 |
| 103 | " | " | 1 | (n-C₃H₇)₄NOH*6 | 1 | 75 | 72 | 96 |
| 104 | Pd Black | I₂ | 1 | DBU*5 | 1 | 92 | 87 | 95 |
| 105 | " | " | 1 | CH₃COOK | 1 | 52 | 44 | 84 |
| 106 | " | " | 1 | (CH₃)₂NLi | 1 | 90 | 86 | 96 |
| 107 | " | " | 1 | NaHCO₃ | 1 | 85 | 80 | 94 |
| 108 | " | " | 1 | K₂CO₃ | 1 | 86 | 79 | 92 |
| 109 | " | " | 1 | Al(OH)₃ | 1 | 53 | 47 | 89 |
| 110 | " | " | 1 | La₂O₃ | 1 | 55 | 47 | 85 |
| 111 | 5% Pd/C | " | 1 | RbOH | 1 | 88 | 84 | 95 |
| 112 | " | " | 1 | (C₂H₅)₃N | 1 | 89 | 85 | 95 |
| 113 | 5% (Pd—Te)/C*2 | " | 1 | RbOH | 1 | 86 | 80 | 93 |
| 114 | " | " | 1 | (C₂H₅)₃N | 1 | 85 | 80 | 94 |
| 115 | 5% Rh/C | " | 1 | (C₂H₅)₃N | 1 | 82 | 75 | 92 |
| 116 | RhI₃ | " | 1 | RbOH | 1 | 73 | 66 | 90 |
| 117 | Ru Black | " | 1 | RbOH | 1 | 58 | 49 | 84 |
| 118 | IrCl₃ | " | 1 | (C₂H₅)₃N | 1 | 48 | 33 | 69 |
| 119 | 5% Pt/C | " | 1 | (C₂H₅)₃N | 1 | 62 | 48 | 78 |

*1%: weight %
*2Lindlar catalyst: 5% by weight (Pd—Pb)/CaCO₃ where the atomic ratio of Pd to Pb is 1:2.
*3(Pd—Te)/C was prepared by supporting palladium chloride and tellurium dioxide at a mol ratio of 10 to 3 on active carbon and then reducing the resultant with hydrogen at 350° C.

*4 $\begin{bmatrix} CO \\ \phantom{x} \\ CO \end{bmatrix} N-$ : succinimido group

*5DBU: 1,8-diazabicyclo-[5,4,0]-undecene-7
*6(n-C₃H₇)₄NOH: 10% by weight aqueous solution of tetra-n-propyl-ammonium hydroxide

EXAMPLE 120

In a 140 ml stirring type autoclave were charged 40 mmols of cyclohexylamine, 40 ml of ethanol, 0.5 mg-atom of palladium black and 2 mmols of cesium iodide. After the air inside the autoclave had been replaced with carbon monoxide, carbon monoxide was pressurized into the autoclave to 80 Kg/cm² and then oxygen was pressurized into the autoclave to 6 Kg/cm², resulting in a total pressure of 86 Kg/cm². The reaction was carried out at 160° C. for one hour with stirring, and subsequently the reaction mixture obtained was subjected to filtration. As the result of analysis of the filtrate, the conversion of cyclohexylamine was 85% and the yield of ethyl N-cyclohexylcarbamate was 81% with a selectivity of 95%.

EXAMPLE 121

The procedure of Example 120 was repeated except that 2 mmols of tetramethylammonium iodide were employed instead of the cesium iodide. As a result, a yellowish filtrate was obtained, and the conversion of cyclohexylamine was 82% and the yield of ethyl N-cyclohexylcarbamate was 80% with a selectivity of 98%. When ethanol was distilled from the filtrate and then tetramethylammonium iodide was removed by washing with water, yellowish crystals were precipitated. The crude crystals thus obtained were ethyl N-cyclohexylcarbamate of 98% purity and recrystallized once from ethanol to give white crystals of ethyl N-cyclohexylcarbamate of 100% purity.

EXAMPLE 122

The procedure of Example 3 was repeated except that 40 mmols of cyclohexylamine were employed instead of the aniline. As a result, the conversion of cyclohexylamine was 85% and the yield of ethyl N-cyclohexylcarbamate was 82% with a selectivity of 97%. Further, the reaction was repeated in the same manner as in Example 3 and the result obtained was as good as the above, i.e., the conversion of cyclohexylamine was 83% and the yield of ethyl N-cyclohexylcarbamate was 81% with a selectivity of 98%.

EXAMPLE 123

The procedure of Example 120 was repeated except that 1 mmol of ethyl iodide, and 1 mmol of N,N,N',N'-tetramethylethylenediamine were employed instead of the cesium iodide and that 40 ml of methanol were employed instead of the ethanol. As a result, the conversion of cyclohexylamine was 88% and the yield of methyl N-cyclohexylcarbamate was 83% with a selectivity of 94%.

EXAMPLE 124

The procedure of Example 120 was repeated except that 1 mmol of potassium metaperiodate was employed instead of the cesium iodide and that 50 ml of methanol were employed instead of the ethanol. As a result, the conversion of cyclohexylamine was 85% and the yield of methyl N-cyclohexylcarbamate was 78% with a selectivity of 92%.

COMPARATIVE EXAMPLE 3

The procedure of Example 120 was repeated except that the cesium iodide was not employed. As a result, the conversion of cyclohexylamine was 10% and the yield of ethyl N-cyclohexylcarbamate was only 3%.

EXAMPLE 125

The procedure of Example 120 was repeated except that 40 mmols of di-n-butylamine were employed instead of the cyclohexylamine and that 2 mmols of methyltriphenylphosphonium iodide were employed instead of the cesium iodide. As a result, the conversion of di-n-butylamine was 85% and the yield of ethyl N,N-n-butylcarbamate was 78% with a selectivity of 92%.

EXAMPLE 126

The procedure of Example 120 was repeated except that 30 mmols of di-n-butylamine were employed instead of the cyclohexylamine and that 1 mmol of iodine and 1 mmol of cesium hydroxide were employed instead of the cesium iodide. As a result, the conversion of di-n-butylamine was 70% and the yield of methyl N,N-di-n-butylcarbamate was 56% with a selectivity of 80%.

EXAMPLE 127

The procedure of Example 120 was repeated except that 15 mmols of 1,6-hexamethylenediamine were employed instead of the cyclohexylamine and that 2 mmols of tetramethylammonium iodide were employed instead of the cesium iodide. As a result, the conversion of 1,6-hexamethylenediamine was 94% and the yield of diethyl 1,6-hexamethylenedicarbamate was 87% with a selectivity of 93%.

EXAMPLE 128

The procedure of Example 120 was repeated except that 40 mmols of benzylamine were employed instead of the cyclohexylamine, that 1 mg-atom of palladium black was employed instead of 0.5 mg-atom of palladium black and that 1 mmol of tetramethylammonium iodide and 1 mmol of triethylamine were employed instead of the cesium iodide. As a result, the conversion of benzylamine was 90% and the yield of ethyl N-benzylcarbamate was 85% with a selectivity of 94%. The selectivity of molecular oxygen to the urethanation was 92%. When the above described procedure was repeated except that the trethylamine was not employed, the selectivity of oxygen to the urethanation was 80%.

EXAMPLE 129

In a 200 ml stirring type autoclave were charged 50 mmols of benzylamine, 50 ml of ethanol, 1 g of 5% by weight rhodium supported on active carbon and 3 mmols of cesium iodide. After the air inside the autoclave had been replaced with carbon monoxide, carbon monoxide was pressurized into the autoclave to 80 Kg/cm$^2$ and oxygen was pressurized into the autoclave to 6 Kg/cm$^2$, resulting in a total pressure of 86 Kg/cm$^2$. The reaction was carried out at 160° C. for one hour with stirring and the reaction mixture obtained was subjected to filtration. As the result of analysis of the filtrate obtained, the conversion of benzylamine was 77% and the yield of ethyl N-benzylcarbamate was 69% with a selectivity of 90%.

EXAMPLE 130

In 500 ml stirring type autoclave were charged 100 mmols of aniline, 150 ml of ethanol, 1 mg-atom of palladium black and 2 mmols of tetraethylammonium iodide. After the air inside the autoclave had been replaced with carbon monoxide, the autoclave was heated to 160° C. and a mixed gas of 70 Kg/cm$^2$ of carbon monoxide and 30 Kg/cm$^2$ of air was continuously fed into the solution mixture in the autoclave at a rate of 0.5 Nl/min. After one hour the reaction was stopped and the reaction solution was subjected to analysis. As a result, the conversion of aniline was 99% and the yield of ethyl N-phenylcarbamate was 97% with a selectivity of 98%.

EXAMPLE 131

In a 300 ml stirring type autoclave were charged 30 mmols of 2,4-diaminotoluene, 50 ml of methanol, 1 g of 10% by weight palladium supported on active carbon and 8 mmols of rubidium iodide. After the air inside the autoclave had been replaced with carbon monoxide, carbon monoxide was pressurized into the autoclave to 120 Kg/cm$^2$ and oxygen was pressurized into the autoclave to 8 Kg/cm$^2$, resulting in a total pressure of 128 Kg/cm$^2$. The reaction was carried out at 160° C. for one hour with stirring and the reaction mixture obtained was subjected to filtration. As the result of analysis of the filtrate obtained, the conversion of 2,4-diaminotoluene was 80% and the yield of dimethyl tolylene-2,4-dicarbamate was 68% and the yield of the aminomonourethane which was a mixture of methyl 3-amino-4-methylcarbanilate and methyl 2-methyl-5-aminocarbanilate was 8%. The total selectivity to the urethanation was 95%.

EXAMPLE 1

In a 300 ml stirring type autoclave were charged 30 mmols of 2,4-diaminotoluene, 50 ml of ethanol, 1 mg-atom of palladium black, 2 mmols of iodoform and 2 mmols of potassium hydroxide. After the air inside the autoclave had been replaced with carbon monoxide, carbon monoxide was pressurized into the autoclave to 100 Kg/cm$^2$ and then oxygen was pressurized into the autoclave to 7 Kg/cm$^2$, resulting in a total pressure of 107 Kg/cm$^2$. The reaction was carried out at 160° C. for one hour with stirring, and subsequently the reaction mixture obtained was subjected to filtration. As the result of analysis of the filtrate, the conversion of 2,4-diaminotoluene was 88% and the yield of diethyl tolylene-2,4-dicarbamate was 74% and the yield of the aminomonourethane which was a mixture of ethyl 3-amino-4-methylcarbanilate and ethyl 2-methyl-4- aminocarbanilate was 11%. The total selectivity to the urethanation was 95%.

EXAMPLE 133

In a 200 ml stirring type autoclave were charged 30 mmols of aniline, 15 mmols of nitrobenzene, 50 ml of methanol, 0.5 mmol of palladium chloride and 5 mmols of tetrabutylammonium iodide. After the air inside the autoclave had been replaced with carbon monoxide, carbon monoxide was pressurized into the autoclave to 140 Kg/cm$^2$, and the reaction was carried out at 180° C. for 3 hours with stirring. As the result of analysis of the reaction solution obtained, the conversions of aniline and nitrobenzene were 20% and 26%, respectively, and 7 mmols of methyl N-phenylcarbamate were obtained.

EXAMPLE 134

In a 200 ml stirring type autoclave were charged 30 mmols of aniline, 15 mmols of nitrobenzene, 50 ml of methanol, 0.5 mmol of palladium chloride and 5 mmols of potassium metaperiodate. After the air inside the autoclave had been replaced with carbon monoxide, carbon monoxide was pressurized into the autoclave to 120 Kg/cm$^2$, and the reaction was carried out at 180° C. for 6 hours with stirring. As the result of analysis of the reaction solution obtained, the conversions of aniline and nitrobenzene were 28% and 34%, respectively, and 8 mmols of methyl N-phenylcarbamate were obtained.

EXAMPLE 135

In a 200 ml stirring type autoclave were charged 30 mmols of aniline, 15 mmols of nitrobenzene, 50 ml of ethanol, 3 mmols of palladium chloride, 3 mmols of tetraiodomethane and 3 mmols of rubidium hydroxide. After the air inside the autoclave had been replaced with carbon monoxide, carbon monoxide was pressurized into the autoclave to 120 Kg/cm$^2$, and the reaction was carried out at 180° C. for 5 hours with stirring. As the result of analysis of the reaction solution, the conversions of aniline and nitrobenzene were 21% and 29%, respectively, and 8 mmols of ethyl N-phenylcarbamate were obtained.

EXAMPLE 136

In a 140 ml stirring type autoclave were charged 20 mmols of N,N'-diphenylurea, 40 ml of ethanol, 0.5 mg-atom of palladium black and 5 mmols of cesium iodide. After the air inside the autoclave had been replaced with carbon monoxide, carbon monoxide was pressurized into the autoclave to 80 Kg/cm$^2$ and then oxygen was pressurized into the autoclave to 6 Kg/cm$^2$, resulting in a total pressure of 86 Kg/cm$^2$. The reaction was carried out at 160° C. for one hour with stirring, and subsequently the reaction mixture obtained was subjected to filtration. As the result of analysis of the filtrate, the conversion of N,N'-diphenylurea was 100% and the yield of ethyl N-phenylcarbamate was 98% with a selectivity of 98%.

EXAMPLE 137

The procedure of Example 136 was repeated except that 5 mmols of tetramethylammonium iodide were employed instead of the cesium iodide. The filtrate obtained was a yellowish solution. As a result, the conversion of N,N'-diphenylurea was 100% and the yield of ethyl N-phenylcarbamate was 99% with a selectivity of 99%.

When ethanol was distilled from this solution under reduced pressure and then tetramethylammonium iodide was removed by washing with water, yellow crystals were precipitated. The crude crystals thus obtained were ethyl N-phenylcarbamate of 99% purity and recrystallized once from ethanol to give white crystals of ethyl N-phenylcarbamate of 100% purity.

EXAMPLE 138

The procedure of Example 136 repeated except that 5 mmols of methyltriphenylphosphonium iodide were employed instead of the cesium iodide. As a result, the conversion of N,N'-diphenylurea was 98% and the yield of ethyl N-phenylcarbamate was 96% with a selectivity of 98%.

EXAMPLE 139

In a N-methylpyrolidone solution containing 10% by weight of m-phenylenediamine was added an equimolar amount of 2,4-pyridinedicarboxylic acid chloride, and the reaction was carried out at a temperature of from 40° C. to 60° C. for 3 hours. The reaction solution thus obtained was added dropwise to a large amount of water with stirring, and the precipitate formed was washed with an aqueous sodium hydroxide solution and with water and then dried to give a pyridine ring-containing aromatic polyamide having units of the formula:

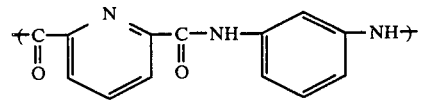

This polymer was treated with methyl iodide to give an iodine-containing polymer having quaternary pyridium iodide groups.

One gram of the iodine-containing polymer thus obtained, 25 mmols of N,N'-diphenylurea, 50 ml of methanol and 0.5 mg-atom of palladium black were charged into a 200 ml stirring type autoclave. After the air inside the autoclave was replaced with carbon monoxide, carbon monoxide was pressurized into the autoclave to 80 Kg/cm$^2$, and subsequently oxygen was pressurized into the autoclave to 6 Kg/cm$^2$, resulting in a total pressure of 86 Kg/cm$^2$. The reaction was carried out with stirring at 160° C. for one hour, and then the reaction mixture was subjected to filtration. As the result of analysis of the filtrate, the conversion of N,N'-diphenylurea was 98% and the yield of ethyl N-phenylcarbamate 96% with a selectivity of 98%.

When the above described procedure was repeated by using the palladium black and the iodine-containing polymer separated by filtration as such, the result obtained was as good as the above, i.e., the conversion of N,N'-diphenylurea was 99% and the yield of ethyl N-phenylcarbamate was 97% with a selectivity of 98%.

EXAMPLE 140

The procedure of Example 136 was repeated except that 1 mmol of potassium metaperiodate was employed instead of the cesium iodide. As a result, the conversion of N,N'-diphenylurea was 96% and the yield of ethyl N-phenylcarbamate was 94% with a selectivity of 98%.

EXAMPLE 141

The procedure of Example 136 was repeated except that 0.25 mmol of potassium tetraiodobismuthate was employed instead of the cesium iodide. As a result, the conversion of N,N'-diphenylurea was 92% and the yield of ethyl N-phenylcarbamate was 87% with a selectivity of 95%.

EXAMPLE 142

The procedure of Example 136 was repeated except that 0.3 mmol of iodoform and 1 mmol of triethylamine were employed instead of the cesium iodide. As a result, the conversion of N,N'-diphenylurea was 95% and the yield of ethyl N-phenylcarbamate was 92% with a selectivity of 97%. In the filtrate obtained no palladium was detected. The selectivity of molecular oxygen to the urethanation was 94%.

When the above described procedure was repeated except that the triethylamine was not employed, the conversion of N,N'-diphenylurea was 85% and the yield of ethyl N-phenylcarbamate was 80% with a selectivity of 94%, and the selectivity of molecular oxygen to the urethanation was 75%.

The reaction solution obtained in either case was transparent and yellowish.

EXAMPLE 143

The procedure of Example 136 was repeated except that 1 mmol of iodine and 1 mmol of triethylamine were employed instead of the cesium iodide. As a result, the conversion of N,N'-diphenylurea was 98% and the yield of ethyl N-phenylcarbamate was 96% with a selectivity of 98%. In the filtrate no palladium was detected.

When the above described procedure was repeated except that the triethylamine was not employed, the conversion of N,N'-diphenylurea was 48% and the yield of ethyl N-phenylcarbamate was 31% with a selectivity of 65%.

COMPARATIVE EXAMPLE 4

The procedure of Example 136 was repeated except that the cesium iodide was not employed. As a result, the conversion of N,N'-diphenylurea was 10% and the yield of ethyl N-phenylcarbamate was only 3%.

COMPARATIVE EXAMPLE 5

The procedure of Example 136 was repeated except that 1 mmol of triethylamine was employed instead of the cesium iodide. As a result, the conversion of N,N'-diphenylurea was 5% and the yield of ethyl N-phenylcarbamate was less than about 1%.

EXAMPLES 144 TO 175

The procedure of Example 136 was repeated except that 0.5 mg-atom of a platinum group metal or a compound containing the platinum group element based on the metal element set forth in Table 2 was employed in the presence or absence of, as an additional promoter, a basic substance set forth in Table 2 instead of the cesium iodide The results are shown in Table 2.

TABLE 2

| Example No. | Pt Group Metal or Compound Containing At Least One Pt Group Element[*1] | Halogen-containing Compound | (mmol) | Basic Substance | (mmol) | C₆H₅-NHCNH-C₆H₅ ‖ O Conversion (%) | C₆H₅-NHCOOC₂H₅ Yield (%) | Selectivity (%) |
|---|---|---|---|---|---|---|---|---|
| 144 | Pd Black | LiCl | 5 | — | | 80 | 70 | 88 |
| 145 | " | KBr | 5 | — | | 88 | 79 | 90 |
| 146 | " | RbI | 5 | — | | 98 | 93 | 95 |
| 147 | " | BaI$_2$.2H$_2$O | 5 | — | | 75 | 69 | 92 |
| 148 | RhI$_3$ | CsI | 5 | — | | 93 | 88 | 95 |
| 149 | Ru Black | " | 5 | — | | 80 | 72 | 90 |
| 150 | 5% Pt/C | " | 5 | — | | 85 | 76 | 89 |
| 151 | Pd Black | NH$_4$Br | 5 | — | | 90 | 83 | 92 |
| 152 | " | [(C$_2$H$_5$)$_4$N]$^⊕$I$^⊖$ | 5 | — | | 98 | 94 | 96 |
| 153 | 5% Pd/C | [(CH$_3$)$_4$N]$^⊕$I$^⊖$ | 5 | — | | 100 | 98 | 98 |
| 154 | RhI$_3$ | " | 5 | — | | 90 | 84 | 93 |
| 155 | Pd Black | [(CH$_3$)$_4$P]$^⊕$I$^⊖$ | 5 | — | | 100 | 96 | 96 |
| 156 | " | [(CH$_3$)$_3$S]$^⊕$I$^⊖$ | 1 | (n-C$_4$H$_9$)$_3$N | 1 | 60 | 48 | 80 |
| 157 | 5% Rh/C | [(C$_6$H$_5$)$_3$PCH$_3$]$^⊕$I$^⊖$ | 5 | — | | 93 | 88 | 95 |
| 158 | 5% (Pd—Te)/C[*2] | [(C$_6$H$_5$)$_3$PCH$_3$]$^⊕$I$^⊖$ | " | — | | 97 | 94 | 97 |
| 159 | Ru Black | " | " | — | | 90 | 82 | 91 |
| 160 | Pd Black | KBrO$_3$ | 1 | — | | 62 | 56 | 90 |
| 161 | " | RbIO$_4$ | 1 | — | | 95 | 92 | 97 |
| 162 | " | HIO$_3$ | 1 | CsOH | 1 | 80 | 74 | 92 |
| 163 | 5% Rh/C | KIO$_4$ | 1 | — | | 82 | 75 | 92 |
| 164 | Ru Black | " | 1 | — | | 70 | 61 | 87 |
| 165 | Pd Black | K$_2$[TeBr$_6$] | 0.2 | — | | 90 | 85 | 94 |
| 166 | " | [(CH$_3$)$_4$N][I$_5$] | 0.2 | — | | 67 | 59 | 88 |
| 167 | " | " | 0.2 | RbOH | 1 | 76 | 68 | 90 |
| 168 | RhI$_3$ | K[BiI$_4$].H$_2$O | 0.25 | — | | 88 | 79 | 90 |
| 169 | 5% Pt/C | " | 0.25 | — | | 85 | 75 | 88 |
| 170 | Pd Black | CH$_3$I | 0.8 | (C$_2$H$_5$)$_3$N | 1 | 92 | 85 | 92 |
| 171 | " | CHI$_3$ | 0.3 | RbOH | 1 | 94 | 89 | 95 |
| 172 | 5% Rh/C | CHI$_3$ | 0.3 | (C$_2$H$_5$)$_3$N | 1 | 90 | 83 | 92 |
| 173 | Pd Black | I$_2$ | 1 | NaHCO$_3$ | 1 | 93 | 91 | 98 |
| 174 | " | " | 1 | RbOH | 1 | 96 | 94 | 98 |
| 175 | 5% Rh/C | " | 1 | (C$_2$H$_5$)$_3$N | 1 | 88 | 84 | 95 |

[*1]%: weight %
[*2](Pd—Te)/C was prepared by supporting palladium chloride and tellurium dioxide at a mol ratio of 10 to 3 on active carbon and then reducing the resultant with hydrogen at 350° C.

EXAMPLE 176

In a 140 ml stirring type autoclave were charged 20 mmols of N,N'-dicyclohexylurea, 40 ml of ethanol, 0.5 mg-atom of palladium black and 2 mmols of cesium iodide. After the air inside the autoclave had been replaced with carbon monoxide, carbon monoxide was pressurized into the autoclave to 80 Kg/cm$^2$ and then oxygen was pressurized into the autoclave to 6 Kg/cm$^2$, resulting in a total pressure of 86 Kg/cm$^2$. The reaction was carried out at 160° C. for one hour with stirring, and subsequently the reaction mixture obtained was subjected to filtration. As the result of analysis of the filtrate, the conversion of N,N'-dicyclohexylurea was 95% and the yield of ethyl N-cyclohexyl carbamate was 93% with a selectivity of 98%.

COMPARATIVE EXAMPLE 6

The procedure of Example 176 was repeated except that the cesium iodide was not employed. As a result, the conversion of N,N'-dicyclohexylurea was 8% and the yield of ethyl N-cyclohexyl carbamate was only 2%.

EXAMPLE 177

The proedure of Example 176 was repeated except that 20 mmols of urea were employed instead of the N,N'-dicyclohexylurea. As a result, the conversion of urea was 85% and the yield of ethyl carbamate was 80% with a selectivity of 94%.

EXAMPLE 178

The procedure of Example 176 was repeated except that 2 mmols of tetramethylammonium iodide were employed instead of the cesium iodide. As a result, a yellowish filtrate was obtained, and the conversion of N,N'-dicyclohexylurea was 96% and the yield of ethyl N-cyclohexyl carbamate was 94% with a selectivity of 98%.

EXAMPLE 179

The procedure of Example 178 was repeated except that 20 mmols of N,N'-di-n-butylurea were employed instead of the N,N'-dicyclohexylurea. As a result, the conversion of N,N'-di-n-butylurea was 94% and the yield of ethyl N-n-butylcarbamate was 88% with a selectivity of 94%.

EXAMPLE 180

The procedure of Example 3 was repeated except that 20 mmols of N,N'-dicyclohexylurea were employed instead of the aniline. As a result, the conversion of N, N'-dicyclohexylurea was 94% and the yield of ethyl N-cyclohexylcarbamate was 90% with a selectivity of 96%. Further, the reaction was repeated in the same manner as in Example 3 and the result obtained was as good as the above, i.e., the conversion of N,N'-dicyclohexylurea was 93% and the yield of ethyl N-cyclohexylcarbamate was 89% with a selectivity of 96%.

EXAMPLE 181

In a 140 ml stirring type autoclave were charged 20 mmols of N,N'-dibenzylurea, 40 ml of ethanol, 1 mg-atom of palladium black and 1 mmol of potassium metaperiodate. After the air inside the autoclave had been replaced with carbon monoxide, carbon monoxide was pressurized into the autoclave to 70 Kg/cm$^2$ and then air was pressurized into the autoclave to 30 Kg/cm$^2$, resulting in a total pressure of 100 Kg/cm$^2$. The reaction was carried out at 160° C. for one hour with stirring, and subsequently the reaction mixture obtained was subjected to filtration. As the result of analysis of the filtrate, the conversion of N,N'-benzylurea was 95% and the yield of ethyl N-benzylcarbamate was 90% with a selectivity of 95%.

EXAMPLE 182

The procedure of Example 181 was repeated except that 1 mmol of tetraiodomethane and 1 mmol of 1,5-diazabicyclo-[4,3,0]-nonene-5(DBN) were employed instead of the potassium metaperiodate. As a result, the conversion of N,N'-dibenzylurea was 95% and the yield of ethyl N-benzylcarbamate was 91% with a selectivity of 96%.

EXAMPLE 183

The procedure of Example 181 was repeated except that 1 mmol of tetraiodomethane was employed instead of the potassium metaperiodate. As a result, the conversion of N,N'-benzylurea was 80% and the yield of ethyl N-benzylcarbamate was 72% with a selectivity of 90%.

EXAMPLE 184

The procedure of Example 176 was repeated except that 20 mmols of N,N'-di-n-butylurea were employed instead of the N,N'-dicyclohexylurea and that 1 mmol of iodine and 1 mmol of potassium hydrogen carbonate were employed instead of the cesium iodide. As a result, the conversion of N,N'-di-n-butylurea was 73% and the yield of ethyl N-n-butylcarbamate was 66% with a selectivity of 90%.

EXAMPLE 185

In a 200 ml stirring type autoclave were charged 30 mmols of N,N'-diphenylurea, 15 mmols of nitrobenzene, 50 ml of methanol, 0.5 mmol of palladium chloride and 5 mmols of tetrabutylammonium iodide. After the air inside the autoclave had been replaced with carbon monoxide, carbon monoxide was pressurized into the autoclave to 140 Kg/cm$^2$, and the reaction was carried out at 180° C. for 5 hours with stirring. As the result of analysis of the reaction solution obtained, the conversions of N,N'-diphenylurea and nitrobenzene were 26% and 33%, respectively, and 15 mmols of methyl N-phenylcarbamate were obtained.

EXAMPLE 186

In a 200 ml stirring type autoclave were charged 30 mmols of N,N'-diphenylurea, 15 mmols of nitrobenzene, 50 ml of methanol, 0.5 mmol of palladium chloride and 5 mmols of cesium iodide. After the air inside the autoclave had been replaced with carbon monoxide, carbon monooxide was pressurized into the autoclave to 120 Kg/cm$^2$, and the reaction was carried out at 180° C. for 4 hours with stirring. As the result of analysis of the reaction solution obtained, the conversions of N,N'-diphenylurea and nitrobenzene were 25% and 30%, respectively, and 14 mmols of methyl N-phenylcarbamate were obtained.

EXAMPLE 187

In a 200 ml stirring type autoclave were charged 30 mmols of N,N'-diphenylurea, 15 mmols of nitrobenzene, 50 ml of methanol, 1 mmol of potassium tetrabromopalladate, 2 mmols of iodine and 2 mmols of triethylamine. After the air inside the autoclave had been replaced with carbon monoxide, carbon monoxide was pressurized into the autoclave to 120 Kg/cm², and the reaction was carried out at 180° C. for 6 hours with stirring. As the result of analysis of the reaction solution, the conversions of N,N'-diphenylurea and nitrobenzene were 30% and 38%, respectively, and 15 mmols of methyl N-phenylcarbamate were obtained.

EXAMPLE 188

In a 200 ml stirring type autoclave were charged 15 mmols of p-phenylenediamine, 80 ml of ethanol, 0.5 mg-atom of palladium black and 1.2 mmols of sodium iodide. After the air inside the autoclave had been replaced with carbon monoxide, carbon monoxide was pressurized into the autoclave to 100 Kg/cm² and then air was pressurized into the autoclave to 30 Kg/cm², resulting in a total pressure of 130 Kg/cm². The reaction was carried out at a temperature of from 160° C. to 170° C. for two hours with stirring. As the result of analysis of the reaction solution obtained, the conversion of p-phenylenediamine was 95% and the yield of diethyl p-phenylenedicarbamate was 88% with a selectivity of 93%.

EXAMPLE 189

The procedure of Example 189 was repeated except that 30 mmols of diphenylamine were employed instead of the p-phenylenediamine. As a result, the conversion of diphenylamine was 83% and the yield of ethyl N,N'-diphenylcarbamate was 70% with a selectivity of 84%.

EXAMPLE 190

In a 140 ml stirring type autoclave were charged 8 mmols of 1,8-diamino-4-aminomethyloctane, 50 ml of trifluoroethanol, 0.5 mg-atom of palladium black and 2 mmols of cesium iodide. After the air inside the autoclave had been replaced with carbon monoxide, carbon monoxide was pressurized into the autoclave to 80 Kg/cm² and then oxygen was pressurized into the autoclave to 6 Kg/cm², resulting in a total pressure of 86 Kg/cm². The reaction was carried out at 200° C. for one hour with stirring. As the result of analysis of the reaction solution obtained, the yield of a triurethane having the following formula:

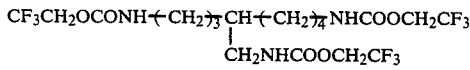

was 94% with a selectivity of 95%.

EXAMPLE 191

The procedure of Example 136 was repeated except that 20 mmols of N-phenyl-N'-p-tolylurea were employed instead of the N,N'-diphenylurea and that 1 mmol of potassium iodide was employed instead of the cesium iodide. As a result, the conversion of N-phenyl-N'-p-tolylurea was 98% and the yield of ethyl N-phenylcarbamate and ethyl N-p-tolylcarbamate was 96%, respectively with a selectivity of 98%, respectively.

EXAMPLE 192

In a 200 ml stirring type autoclave were charged 50 mmols of aniline, 60 ml of cyclohexanol, 1 mg-atom of palladium black and 2 mmols of potassium iodide. After the air inside the autoclave had been replaced with carbon monoxide, carbon monoxide and hydrogen were pressurized into the autoclave to 120 Kg/cm² and 1.5 Kg/cm², respectively and then air was pressurized into the autoclave to 40 Kg/cm². The reaction was carried out at a temperature of from 150° C. to 170° C. for one hour with stirring, and subsequently the reaction mixture obtained was subjected to filtration. As the result of analysis of the filtrate, the conversion of aniline was 98% and the yield of cyclohexyl N-phenylcarbamate was 95% with a selectivity of 97%.

When the above described procedure was repeated except that the hydrogen was not employed, the conversion of aniline was 99% and the yield of cyclohexyl N-phenylcarbamate was 96% with a selectivity of 97%.

This Example shows that a small amount of hydrogen present does not affect the urethanation reaction according to this invention.

EXAMPLE 193

In a 200 ml stirring type autoclave were charged 50 mmols of aniline, 50 mmols of nitrobenzene, 60 mmols of methanol, 2 mmols of palladium chloride and 5 mmols of sodium iodide. After the air inside the autoclave had been replaced with carbon monoxide, carbon monoxide and hydrogen were pressurized into the autoclave to 130 Kg/cm², and 12 Kg/cm², respectively, resulting in a total pressure of 142 Kg/cm². The reaction was carried out at 200° C. for 3 hours with stirring. As the result of analysis of the reaction solution obtained, 68 mmols of methyl N-phenylcarbamate were formed, and 17 mmols of aniline and 10 mmols of nitrobenzene were unreacted. The selectivity of methyl N-phenylcarbamate from aniline and nitrobenzene was 93%.

The foregoing examples illustrate, without limitation, the catalyst and process of the present invention. It is understood that changes and variations can be made in the examples without departing from the spirit and scope of the invention as defined in the following claims.

We claim:

1. A process for producing a urethane compound by oxidative urethanation which comprises reacting at least one compound selected from the group consisting of a primary amine, a secondary amine and a urea compound with carbon monoxide and an organic hydroxyl compound in a reaction medium free of Lewis Acid redox reactants in the presence of a catalyst system comprising:
   (a) at least one member selected from the group consisting of platinum group metals and compounds containing at least one platinum group element, and
   (b) at least one halogen-containing compound selected from the group consisting of alkali or alkaline earth metal halides, onium halides in which a halide ion is electrovalently bound to a cation, compounds capable of forming onium halides in the reaction, oxo acids of halogen atoms and their salts, halogen molecules and organic halides in which there is a halogen atom covalently bound to a carbon selected from the group consisting of aliphatic, aromatic, alicyclic, arylaliphatic, heterocyclic and acid halides, in the presence of molecular oxygen and/or an organic nitro compound as an oxidizing agent at a temperature of from about 80° C. to about 300° C. under a pressure of from about 1 Kg/cm$^2$ to about 500 Kg/cm$^2$.

2. Process of claim 1 wherein the catalyst system comprises at least one basic substance (c) as the additional promoter.

3. Process of claim 2 wherein the basic substance is an alkali or alkaline earth metal, an oxide, hydroxide, carbonate or hydrogencarbonate of an alkali or alkaline earth metal or a tertiary amine.

4. Process of claim 1 wherein the halogen atom in the halogen-containing compound is chlorine, bromine or iodine.

5. Process of claim 4 wherein the halogen atom is bromine.

6. Process of claim 4 wherein the halogen atom is iodine.

7. Process of claim 2 wherein the halogen atom of the halogen-containing compound is chlorine, bromine or iodine.

8. Process of claim 7 wherein the halogen atom is bromine.

9. Process of claim 7 wherein the halogen atom is iodine.

10. Process of claim 1 wherein the platinum group metal or the platinum group element in the compound containing at least one platinum group element is palladium or rhodium.

11. Process of claim 10 wherein the platinum group metal or the platinum group element is palladium.

12. Process of claim 2 wherein the platinum group metal or the platinum group element in the compound containing at least one platinum group element is palladium or rhodium.

13. Process of claim 12 wherein the platinum group metal or the platinum group element is palladium.

14. Process of claim 1 wherein the platinum group metal or the compound containing at least one platinum group element is employed in its solid state.

15. Process of claim 2 wherein the platinum group metal or the compound containing at least one platinum group element is employed in its solid state.

16. Process of claim 1 wherein the amount of the platinum group metal or the platinum group element in the compound containing at least one platinum group element is about 0.0001% by mol to about 50% by mol per mol of the primary or secondary amine and/or urea compound.

17. Process of claim 2 wherein the amount of the platinum group metal or the platinum group element in the compound containing at least one platinum group element is about 0.0001% by mol to about 50% by mol per mol of the primary or secondary amine and/or urea compound.

18. Process of claim 1 wherein the halogen-containing compound is an alkali or alkaline earth metal halide.

19. Process of claim 1 wherein the halogen-containing compound is an onium halide or a compound capable of forming an onium halide in the reaction.

20. Process of claim 19, wherein the onium halide is a quaternary ammonium halide.

21. Process of claim 19 wherein the onium halide is a polymer having an onium halide group.

22. Process of claim 1 wherein the halogen-containing compound is an oxo acid of a halogen atom or its salt.

23. Process of claim 2 wherein the halogen-containing compound is an organic halide selected form the group consisting of aliphatic, alicyclic, arylaliphatic, heterocyclic and acid halides.

24. Process of claim 2 wherein the halogen-containing compound is a halogen molecule.

25. Process of claim 1 wherein the amount of the halogen atom in the halogen-containing compound is about 0.001 mol to about 10,000 mols per mol of the platinum group metal element in the platinum group metal or compound containing at least one platinum group element.

26. Process of claim 2 wherein the amount of the halogen atom in the halogen-containing compound is about 0.001 mol to about 10,000 mols per mol of the platinum group metal element in the platinum group metal or compound containing at least one platinum group element.

27. Process of claim 2 wherein the amount of the basic compound (c) is about 0.01 mol to about 1,000 mols per halogen atom in the halogen-containing compound (b).

28. Process of claim 1 wherein the oxidizing agent is molecular oxygen.

29. Process of claim 2 wherein the oxidizing agent is molecular oxygen.

30. Process of claim 1 wherein carbon monoxide containing less than about 10% by mol of hydrogen is used.

31. Process of claim 2 wherein carbon monoxide containing less than about 10% by mol of hydrogen is used.

32. Process of claim 1 wherein the organic hydroxyl group is a $C_{1-10}$ aliphatic monoalcohol, a $C_{3-10}$ alicyclic monoalcohol or a $C_{7-15}$ aralkyl monoalcohol.

33. Process of claim 1 wherein the primary amine is an aromatic primary amine.

34. Process of claim 33 wherein the aromatic primary amine is aniline.

35. Process of claim 1 wherein the urea compound is a N,N'-di-substituted urea.

36. Process of claim 35 wherein the N,N'-di-substituted urea is N,N'-diphenylurea.

37. Process of claim 2 wherein the organic hydroxyl group is a $C_{1-10}$ aliphatic monoalcohol, a $C_{3-10}$ alicyclic monoalcohol or a $C_{7-15}$ aralkyl monoalcohol.

38. Process of claim 2 wherein the primary amine is an aromatic primary amine.

39. Process of claim 38 wherein the aromatic primary amine is aniline.

40. Process of claim 2 wherein the urea compound is a N,N'-di-substituted urea.

41. Process of claim 40 wherein the N,N'-di-substituted urea is N,N'-diphenylurea.

* * * * *